US005530179A

United States Patent [19]
Terhorst et al.

[11] Patent Number: 5,530,179
[45] Date of Patent: Jun. 25, 1996

[54] TRANSGENIC IMMUNODEFICIENT ANIMAL MODELS

[75] Inventors: Cornelius P. Terhorst, Cambridge; Baoping Wang, Boston, both of Mass.

[73] Assignee: Beth Israel Hospital Association, Boston, Mass.

[21] Appl. No.: 26,388

[22] Filed: Mar. 3, 1993

[51] Int. Cl.$^6$ ............................ C12N 15/00; A61K 49/00
[52] U.S. Cl. ................ 800/2; 800/DIG. 1; 800/DIG. 2; 800/DIG. 3; 424/9.2; 424/93.7; 435/172.3
[58] Field of Search .............................. 800/2, DIG. 1–3; 435/172.3; 935/111; 424/9, 93.7, 577, 573, 9.2

[56] References Cited

U.S. PATENT DOCUMENTS 5,175,384  12/1992  Krimpenfort et al. ....................... 800/2

FOREIGN PATENT DOCUMENTS

WO90/06359  6/1990  WIPO.
WO92/03918  3/1992  WIPO.

OTHER PUBLICATIONS

Ashwell et al., "Genetic And Mutational Analysis Of The T–Cell Antigen Receptor," Annu. Rev. Immunol. 8:139–167, 1990.
Baniyash et al., "Disulfide Linkage Of The ζ And η Chains Of The T Cell Receptor," The Journal of Biological Chemistry 263:9874–9878, 1988.
Barry et al., "Successful Engraftment Of Human Postnatal Thymus In Severe Combined Immune Deficient (SCID) Mice: . . . Immunosuppressive Regimens," J. Exp. Med. 173:167–180, 1991.
Biron et al., "Murine Natural Killer Cells Stimulated In Vivo Do Not Express The T Cell Receptor α, β, γ, T3δ, Or T3ε Genes," The Journal of Immunology 139:1704–1710, 1987.
Blumberg et al., "Structure Of The T–Cell Antigen Receptor: Evidence For Two CD3 ε Subunits In The T–Cell Receptor–CD3 Complex," Proc. Natl. Acad. Sci. USA 87:7220–7224, 1990.
Brombacher et al., "Elimination of CD8+0 Thymocytes In Transgenic Mice Expressing An Anti–LYT2.2 Immuno-–Globulin Heavy Chain Gene," The Embo Journal 8:3719–3726, 1989.
Clevers et al., "Characterization And Expression Of The Murine CD3–ε Gene," Proc. Natl. Acad. Sci. USA 85:98623–8627, 1988.
Clevers et al., "An Enhance Located In A CpG–Island 3' To The TCR/CD3–ε Gene Confers T Lymphocyte–Specificity To Its Promoter," The EMBO Journal 8:2527–2535, 1989.
Clevers et al., "Human CD3–ε Gene Contains Three Miniexons And Is Transcribed From A Non–Tata Promoter," Proc. Natl. Acad. Sci. USA 85:8156–8160, 1988.
Correa et al., "Most γδ T Cells Develop Normally In β$_2$–Microglobulin–Deficient Mice," Proc. Natl. Acad. Sci. USA 89:653–657, 1992.
Cosgrove et al., "Mice Lacking MHC Class II Molecules," Cell 66:1051–1066, 1991.

de la Hera et al., "Structure Of The T Cell Antigen Receptor (TCR): Two CD3ε Subunits In A Functional TCR/CD3 Complex," J. Exp. Med. 173:7–17, 1991.
Finkel et al., "The Thymus Has Two Functionally Distinct Populations Of Immature αβ+ T Cells: One Population Is Deleted By Ligation of αβTCR,"Cell 58:1047–1054, 1989.
Finkel et al., "Immature Thymocytes Are Protected From Deletion Early In Ontogeny," Proc. Natl. Acad. Sci. USA 89:3372–3374, 1992.
Finkel et al., "T–Cell Development And Transmembrane Signaling: Changing Biological Responses Through An Unchanging Receptor," Immunology Today 12:79–85, 1991.
Gold et al., "Evolutionary Relationship Between The T3 Chains Of The T3 Chains Of The T–Cell Receptor Complex And The Immunologlobulin Supergene Family," Proc. Natl. Acad. Sci. USA 84:7649–7653, 1987.
Gold et al., "Isolation Of cDNA Clones Encoding The 20K Non–Glycosylated Polypeptide Chain Of The Human T–Cell Receptor/T3 Complex," Nature 321:431–434, 1986.
Grusby et al., "Depletion Of CD4+ T Cells In Major Histocompatibility Complex Class II–Deficient Mice," Science 253:1417–1420, 1991.
Hanahan, "Transgenic Mice As Probes Into Complex System," Science 246:1265–1275, 1989.
Huesmann et al., "Kinetics And Efficacy Of Positive Selection In The Thymus Of Normal And T Cell Receptor Transgenic Mice," Cell 66:533–540, 1991.
Kamel–Reid et al., "A Model Of Human Acute Lymphoblastic Leukemia In Immune–Deficient SCID Mice," Science 246:1597–1600, 1989.
Kamel–Reid et al., "Engraftment Of Immune–Deficient Mice With Human Hematopoietic Stem Cells," Science 242:1706–1709, 1988.
Kelley, "Gene Therapy In Humans: A New Era Begins," Annals of Internal Medicine 114:697–698, 1991.
Kishi et al., "Surface Expression Of The β T Cell Receptor (TCR) Chain In The Absence Of Other TCR Or CD3 Proteins On Immature T Cells," The EMBO Journal 10;93–100, 1991.
Kisielow et al., "Tolerance In T–Cell–Receptor Transgenic Mice Involves Deletion Of Nonmature CD4+8+ Thymocytes," Nature 333:742–746, 1988.
Klausner et al., "T Cell Antigen Receptor Activation Pathways: The Tyrosine Kinase Connection" Cell 64:875–878, 1991.
Koller et al., "Normal Development Of Mice Deficient In β$_2$M, MHC Class I Proteins, And CD 8+ T Cells," Science 248:1227–1230, 1990
Krimpenfort et al., "T Cell Depletion In Transgenic Mice Carrying A Mutant Gene For TCR–β," Nature 341:742–746, 1989.

(List continued on next page.)

*Primary Examiner*—Jasemine C. Chambers
*Attorney, Agent, or Firm*—Fish & Richardson

[57] ABSTRACT

The invention features a transgenic mouse having a substantial deficiency in functionally active natural killer cells and T lymphocytes which is useful as a model system for immune diseases, tumorigenesis and transplant rejection.

28 Claims, 20 Drawing Sheets

OTHER PUBLICATIONS

Kruisbeek et al., "Early Development Of The T Cell Repertoire," Journal of Experimental Medicine 157:1932–46, 1983.

Kruisbeek et al., "Absence Of The LYT-2⁻,L3T4+ Lineage Of T Cells In Mice Treated Neonatally . . . With I-A-Bearing Antigen-Presenting Cell Function," Journal of Experimental Medicine 161:1029–1047, 1985.

Kyoizumi et al., "Implantation And Maintenance Of Functional Human Bone Marrow In SCID–Hu Mice," Blood 79:1704–1711, 1992.

Lanier et al., "The Developmental Relationship Between NK Cells And T Cells," Immunology Today 13:392–395, 1992.

Lanier et al., "Expression Of Cytoplasmic CD3ε Proteins In Activated Human Adult Natural Killer (NK) Cells And CD3γ,δ,ε Complexes In Fetal NK Cells," The Journal of Immunology 149:1876–1880, 1992.

Lanier et al., "C0–Association Of CD3ζ With A Receptor (CD16) For IgG Fc On Human Natural Killer Cells" Nature 342:803–805, 1989.

Lesley et al., "The Pgp-1 Antigen Is Expressen On Early Fetal Thymocytes," Immunogenetics 22:149–157, 1985.

Letourneur et al., "Activation Of T Cells by A Tyrosine Kinase Activation Domain In The Cytoplasmic Tail Of CD3ε," Science 255:79–82, 1992.

Marusic-Galesic et al., "Development Of CD4[31] CD8+ Cytotoxic T Cells Requires Interactions With Class I MHC Determinants," Nature 333:180–183, 1988.

McCune et al., "The SCID–hu Mouse: Murine Model for The Analysis Of Human Hematolymphoid Differentiation And Function," Science 241:1632–1639, 1988.

McGarry et al., "The Cooperative Effect Of The Satin and Beige Mutations In The Suppression Of NK And CTL Activities In Mice," Immunogenetics 20:527–534, 1984.

Mercep et al., "Activation–Driven Programmed Cell Death And T Cell Receptor ζη Expression," Science 246:1162–1165, 1989.

Mombaerts et al., "Mutations In T–Cell Antigen Receptor Genes α And β Block Thymocyte Development At Different Stages," Nature 360:225–231, 1992.

Mombaerts et al., "RAG-1 Deficient Mice Have No Mature B And T Lymphocytes," Cell 68:869–877, 1992.

Mosier et al., "Transfer Of A Functional Human Immune System To Mice with Severe Combined Immunodeficiency," Nature 335:256–259, 1988.

Mosier et al., "Human Immunodeficiency Virus Infection Of Human–PBL14 SCID Mice," Science 251:791–794, 1991.

Mosier, "Immunodeficient Mice Xenografted With Human Lymphoid Cells: New Models For In Vivo Studies Of Human Immunobiology And Infectious Diseases," J. of Clinical Immunology 10:185–191, 1990.

Murphy et al., "Induction By Antigen Of Intrathymic Apoptosis Of CD4+CD8+TCR[1o] Thymocytes In Vivo," Science 250:1720–1723, 1990.

Namikawa et al., "Infection Of The SCID–hu Mouse By HIV–1," Science 242:1684–1686, 1988.

Peault et al., "Lymphoid Reconstitution Of The Human Fetal Thymus In SCID Mice With CD34+ Precursor Cells," J. Exp. Med. 174:1283–1286, 1991.

Pereira et al., "Blockade Of Transgenic γδ T Cell Development In β₂–Microglobulin Deficient Mice," the Embo Journal 11:25–31, 1992.

Perussia et al., "Murine Natural Killer Cells Express Functional FcγRα Gene," J. Exp. Med. 170:73–86, 1989.

Phillips et al., "Ontogeny Of Human Natural Killer (NK) Cells: Fetal NK Cells Mediate Cytolytic Function And Express Cytoplasmic CD3ε,δ Proteins," J. Exp. Med. 175:1055–1066, 1992.

Philpott et al.,"Lymphoid Development In Mice Congenitally Lacking T Cell Receptor αβ –Expressing Cells," Science 256:1448–1452, 1992.

Reth, "Antigen Receptor Tail Clue," Nature 338:383–384, 1989.

Roder et al., "The Beice Mutation In The Mouse Selectively Impairs Natural Killer Cell Function," Nature 278:451–453, 1979.

Rodewald et al., "A Population Of Early Fetal Thymocytes Expressing FcγRll/lll Contains Precursors Of T Lymphocytes An Natural Killer Cells," Cell 69:139–150, 1992.

Schorle et al., "Development And Function Of T Cells In Mice Rendered Interleukin–2 Deficient By Gene Targeting," Nature 352:621–624, 1991.

Scollay et al., "Development Status And Reconstitution Potential of subpopulations Of Murine Thymocytes," In Immunological Reviews, No. 104, pp. 81–120, Goran Moller, ed., Copenhagen: Munksgaard, 1988.

Sha et al., "Positive And Negative Selection Of An Antigen Receptor On T Cells In Transgenic Mice," Nature 336:73–76, 1988.

Shinkai et al., "Restoration Of T Cell Development In RAG–2–Deficient Mice By Functional TCR Transgenes," Science 259:822–825, 1993.

Shinkai et al., "RAG–2–Deficient Mice Lack Mature Lymphocytes Owing To Inability To Initiate V(D)J Rearrangement," Cell 68:855–867, 1992.

Strasser et al., "bcl–2 Transgene Inhibits T Cell Death and Perturbs Thymic Self–Censorship," Cell 889–899, 1991.

Tiberghien et al., "Anti–Asialo GM1 Antiserum Treatment Of Lethally Irradiated Recipients Before Bone Marrow Transplantaton: Evidence . . . And Hematopoietic Recovery," Blood 76:1419–1430, 1990.

Van Kaer et al., "TAP1 Mutant Mice Are Deficient In Antigen Presentation, Surface Class 1 Molecules, And CD4⁻8[30] T Cells," Cell 71:1205'1241, 1992.

von Boehmer et al., "Self–Nonself Discrimination By T Cells," Science 248:1369–1373, 1990.

von Boehmer, "Thymic Selection: A Matter Of Life And Death," Immunology Today 13:454–458, 1992.

Zijlstra et al., "β2–Microglobulin Deficient Mice Lack CD4⁻8+ Cytolytic T Cells," Nature 344:742–746, 1990.

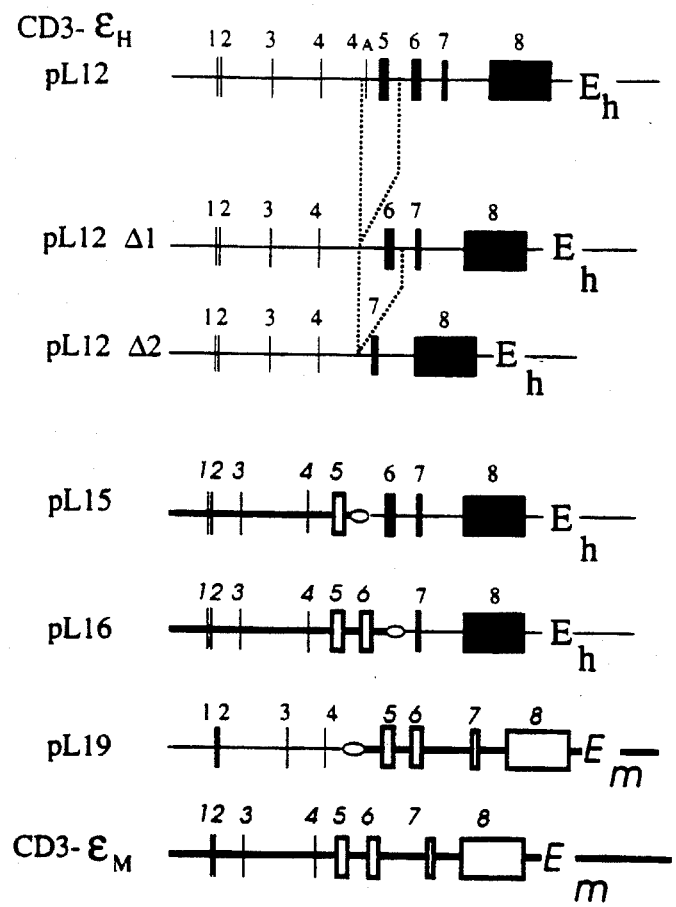
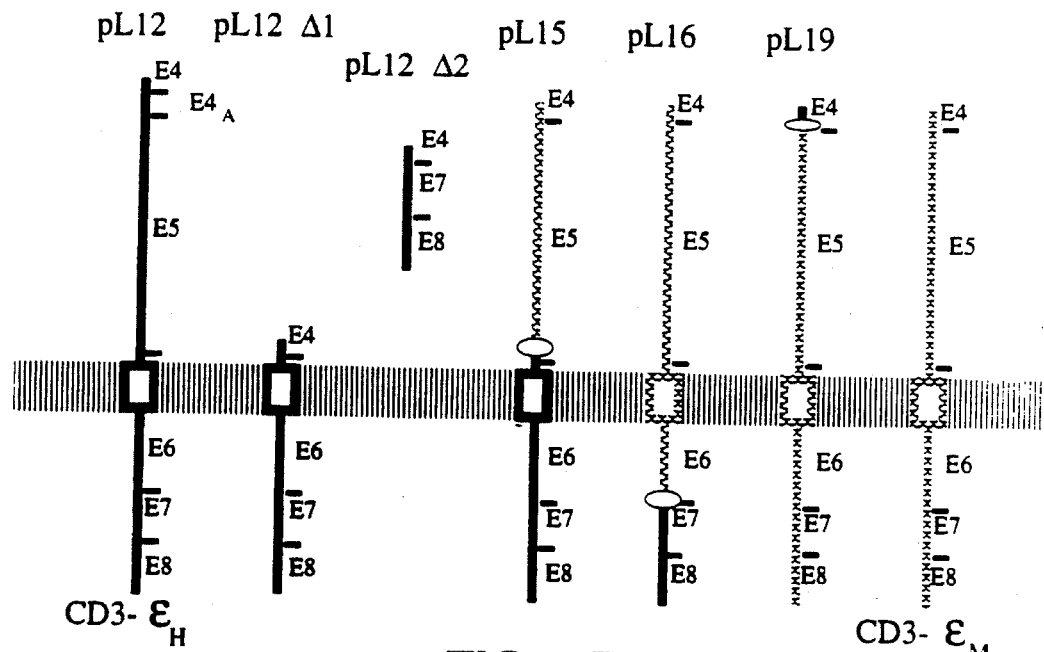
FIG. 1A
FIG. 1B

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 320
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
AAGGTACGGA  AGAGGACGGT  GGCGGTGGAA  GCCGGGCTTG  GAGATGGGAC  ACAGATTTCC   60
ACAAGCTGCC  TGGAAAAGCT  GCGAGCCAGG  GCTGGGGAAG  TGAAGGAGGG  AGGTGTCTCA  120
AGCAGGCACA  CCCCCACCCT  GAGGCAGCCG  CCTGCAGCCA  GAGGCGGGCT  GTGGTTAAGC  180
AGCGCAGGAT  GTGGGCTGCA  CTGCTAAGCG  TGGCTTCTGG  GAGTGAGGGT  GGGAGAGGTA  240
CAGCGGCAGC  TGGCGGAGGC  CCGTGTGAGA  GCGCTTTGTT  CTCAGTCTCC  CACAGCACAC  300
TCTGCTTGCA  GAGGGGGATC                                                 320
```

TRANSGENIC IMMUNODEFICIENT ANIMAL MODELS

BACKGROUND OF THE INVENTION

The field of the invention is transgenic animals.

The vertebrate immune system can be functionally divided into cell compartments providing both adaptive immunity and innate immunity.

Innate immunity is characterized by a lack of specific recognition of particular foreign agents and provides the first line of defense against foreign pathogens, such as viruses, bacteria and protozoa. Cells of the innate immune system, while unable to specifically recognize foreign pathogens, are adept at distinguishing normal, healthy host cells from infected, damaged or transformed host cells, and selectively killing these abnormal cells. In the case of infected cells, cell death is accompanied by destruction of the pathogen's refuge, and in the case of viral infections, often the interruption of nascent viral particle synthesis. For example, the ability of natural killer (NK) cells to efficiently distinguish healthy host "self" cells from infected or otherwise "nonself" cells and to effectively kill the latter accounts for the significant role these lymphoid cells play in tissue graft and transplant rejection.

Adaptive immunity is a complex defense system that is also able to recognize and kill invading organisms such as bacteria, viruses, and fungi, but reacts to foreign antigens with a cascade of molecular and cellular events that ultimately results in the humoral and cell-mediated immune response. This pathway of the immune defense generally commences with the trapping of the antigen by antigen presenting cells (APCS), such as dendritic cells and macrophages. These cells are capable of internalizing, partially digesting, and displaying the "processed" antigen on their cell surfaces. The adaptive immune response of the vertebrate system relies, in part, on cells of the lymphoid line. These cells include B cells, which give rise to soluble antibodies, and T cells, including T helper, T suppressor, and cytotoxic T cells.

T lymphocytes recognize processed antigen in the context of one of two classes of self Major Histocompatibility Complex (MHC) molecules, Class I and Class II. These proteins are the "antigen presenting" proteins found on the surface of APCs. Specific recognition of the APC is accomplished by means of the T-cell antigen receptor (TCR) and either a CD8 protein, specific for Class I MHC and expressed on the surface of cytotoxic (T8) T-cells, or a CD4 protein, specific for class II MHC and expressed on the surface of helper (T4) T-cells. Thus, two different types of T cells are involved in antigen recognition within the context of self MHC (major histocompatibility loci). Mature T helper cells (CD4$^+$ CD8$^-$) recognize antigen in the context of class II MHC molecules, whereas cytotoxic T cells (CD4$^-$ CD8$^+$) recognize antigen in the context of class I MHC determinants.

The TCR is noncovalently associated with CD3$\zeta$, itself a noncovalently associated complex of 5 invariant polypeptide chains; namely, $\gamma$, $\delta$, $\epsilon$, and either a $\zeta\zeta$ homodimer or a $\zeta\eta$ heterodimer (Ashwell, et al. (1990) *Ann. Rev. Immunol.* 8: 139–67). Similarly, NK cells display on their surface a receptor for the Fc portion of IgG, known as Fc$\gamma$RIII. CD3$\zeta$ has also been identified on NK cells and reportedly shown to specifically associate with Fc$\gamma$RIII (Lanier et al. *Nature* 342: 803–805, 1989).

Naturally-occurring immunodeficient mice have been used to study the immune system, cancer, and infectious diseases, including acquired immune deficiency syndrome or AIDS. Several different strains with quite distinct immunodeficient phenotypes have been widely used in these studies. For example, the nude (NU) mouse is athymic, so T cell differentiation and maturation cannot occur. Nude mice have served for many years as host for xenografts, especially human tumors and the testing of anti-cancer drugs. The severe combined immunodeficiency syndrome (SCID) mouse appears to defectively rearrange both TCR (T cell receptor) and immunoglobulin genes and displays a severe immunodeficiency. The beige (BG) mouse carries a defect in functional natural killer cells, whereas the X-linked immunodeficient (XID) mouse has a defect in the production of B cells. In addition, crosses have been made among various strains to generate lines with more comprehensive immunodeficient pheno-types (e.g., BG/NU and BG/NU/XID).

Unfortunately, available immunodeficient mouse strains do not tolerate all transplants. Neither do all grafts maintain the phenotypes observed in the original host. Despite the survival of most human tumors in nude mice, many are nevertheless subject to immune rejection.

A recent attempt to generate an animal model to study AIDS and bone marrow cell differentiation has been reported in which human lymphocytes are transiently proliferated upon coengrafting human fetal liver, thymus, and lymph nodes into SCID mice to form a SCID/nu mouse (McCune et al. (1988) *Science* 241: 1632–1686). Human immune tissues in these mice are susceptible to human immunodeficiency virus (HIV) infection (Namikawa et al. (1988) *Science* 242: 1684–1686) and the model has recently been used to test the effectiveness of AZT in delaying the replication of the AIDS virus. These mice, however are quite limited in their ability to sustain long term engraftment and to support development of multiple human immune tissues. Furthermore, experiments which either human peripheral blood lymphocytes (D. Modier, et al. (1988) *Nature* 335: 256–259), human bone marrow (S. Kamel-Reid, et al. (1988) *Science* 242: 1706–1709) or human bone marrow plus neonatal thymus (Barry, T. S. et al. (1991) *J. Exp. Med.* 173: 167–180) were engrafted into immunodeficient mice have also led to partial transient reconstitution of human lymphocytes.

Because of the above limitations of naturally occurring immunodeficient mice, investigators have attempted to experimentally generate immunodeficient mice by inactivating specific cell lineages or gene function during mouse development.

It has been reported that class II-specific CD4+ CD8- helper T cells (also referred to as T4 cells) fail to develop in mice neonatally treated with anti-class II MHC monoclonal antibody (Kruisbeek, A. N., et al. (1983) *J. Exp. Med.* 157: 1932–1946; Kruisbeek, A. N., et al. (1985) *J. Exp. Med.* 161: 1029–1047). Similarly, it has recently been reported that mice chronically treated with anti-class I MHC monoclonal antibody from firth have significantly reduced population of CD4-CD8+ cells in cytotoxic T cell precursors (Marusic-Galesic, S., et al. (1988) *Nature* 333: 180–183).

A transgenic mouse line has also been constructed containing a transgene encoding a rearranged $\beta$-chain of the TCR wherein the variable region was deleted (Krimpenfort, et al. (1989) *Nature* 341: 742–746). This resulted in a transgenic mouse depleted in mature splenic T-lymphocytes. See also PCT Publication WO 90-06359.

SUMMARY OF THE INVENTION

In general, the invention features a transgenic non-human mammal which has a substantial deficiency in functionally active natural killer cells and T lymphocytes. Preferably, the genome of the transgenic mammal contains at least 30 copies of a transgene which promotes the deficiency. More preferably the genome of the transgenic mammal contains at least 50 copies, and may contain 100–200 or more copies of the transgene. Most preferably the transgenic mammal is homozygous for the transgene.

In other preferred embodiments, the transgene includes a nucleic acid encoding the transmembrane and cytoplasmic domains of a CD3-ε protein operably-linked to a CD3-ε enhancer. The nucleic acid encoding the cytoplasmic and transmembrane domains of a CD3-ε protein from any animal containing a biologically active CD3-ε protein may be used in the invention. Most preferably, the nucleic acid encodes domains from human or mouse CD3-ε. Also preferably, the CD3-ε enhancer includes the E1 domain of the human CD3-ε enhancer; even more preferably the CD3-ε also includes the E2 domain of the human CD3-ε enhancer; and most preferably, the CD3-ε enhancer is a human CD3-ε enhancer with a nucleic acid sequence substantially homologous to the sequence of SEQ ID NO: 1.

In one related aspect, the invention features a method of producing a transgenic non-human mammal having a substantial deficiency in natural killer cells and T lymphocytes. The method includes the steps of introducing a transgene which is capable of promoting the deficiency into an embryonal cell of a non-human mammal, and then obtaining progeny containing the transgene stably incorporated into the genome, wherein the progeny demonstrate the deficiency in natural killer cells and T lymphocytes. Preferably, the method also includes the step of mating the progeny which have the deficiency to produce a transgenic non-human mammal which is homozygous for the transgene.

In a second aspect, the invention features a non-human transgenic mammal which is substantially deficient in natural killer cells, T lymphocytes, and functionally active B lymphocytes, and methods for producing these mammals. Preferably, the animals of this aspect of the invention are produced by introducing a transgene which is capable of promoting deficiency in natural killer cells and T lymphocytes into an embryonal cell of a non-human mammal which is substantially deficient in B lymphocytes, and then obtaining progeny which demonstrate a substantial deficiency in natural killer cells, T lymphocytes and B lymphocytes. Alternatively, a transgenic non-human mammal which has a deficiency in natural killer cells and T lymphocytes may be mated with an animal which is deficient in B lymphocytes to obtain progeny which contain a deficiency in all three cell types. Preferred B lymphocyte deficient animals include those which contain a mutation in the RAG-1 gene or RAG-2 gene.

In a third aspect, the invention features a mammalian model for human immune disease, wherein the model is a transgenic non-human mammal which is deficient for functionally active natural killer cells and T lymphocytes and further characterized in that the transgenic mammal contains human bone marrow cells from a patient with the immune disease. The animal model of this aspect of the invention is useful for studying diseases of the immune system which result in immunodeficiency (e.g., AIDS) and for studying autoimmune diseases, especially systemic autoimmune diseases including Inflammatory Bowel Disease, rheumatoid arthritis, Systemic lupus erythematosus, Scleroderma, Polymyositis, and Sjogren's syndrome.

Accordingly, this aspect of the invention also features a method of testing a substance for efficacy in the treatment of an immune disease. The method includes, exposing a transgenic non-human mammal which is deficient for functionally active natural killer cells and T lymphocytes and which contains human bone marrow cells from a patient with the immune disease to the substance, and then determining the disease progression in the transgenic mammal. An arrest, delay or reversal in disease progression in animals treated with the substance as compared to untreated animals is indicative that the substance is useful for the treatment of the immune disease.

In a fourth aspect, the invention features a mammalian model for a neoplasm, wherein the model is a transgenic non-human mammal which is deficient in functionally active natural killer cells and T lymphocytes and which contains neoplastic cells from a patient with the neoplasm.

Included in this aspect of the invention is a method of testing the efficacy of an anti-neoplastic therapy. The method includes exposing a transgenic non-human mammal which is deficient in functionally active natural killer cells and T lymphocytes and which contains neoplastic cells from a patient with the neoplasm to the therapy, and then determining the progression or growth of the neoplasm in the mammal. An arrest, delay or reversal in neoplastic cell growth in animals exposed to the therapy as compared to untreated animals is indicative that the therapy is useful for the treatment of the neoplasm.

In still another aspect, the invention features a mammalian model for examining tissue graft rejection, wherein the model is a transgenic non-human mammal which is deficient for functionally active natural killer cells and T lymphocytes and contains xenographic tissue, e.g., cells from a different species or strain, such as hematopoietic stem cells, peripheral blood lymphocytes, bone marrow, fetal tissue, organs, and the like.

"Transgenic" as used herein means a mammal which includes a DNA sequence which is inserted by artifice into a cell and becomes part of the genome of the animal which develops from that cell. Such a transgene may be partly or entirely heterologous to the transgenic animal. In the transgenic animals described herein, the DNA sequence is used to promote a deficiency in functionally active natural killer cells and thymocytes. The transgenic animals thus produced are "substantially deficient" in natural killer cells and thymocytes, meaning that the animals exhibit undetectable levels of functionally active natural killer cells and T lymphocytes using standard techniques of immunochemistry such as those described herein. Any non-human mammal which may be produced by transgenic technology is included in the invention; preferred mammals include, in addition to mice, rats, cows, pigs, sheep, goats, rabbits, guinea pigs, hamsters, and horses.

By "transgene" is meant DNA which is partly or entirely heterologous (i.e., foreign) to the transgenic animal, or DNA homologous to an endogenous gene of the transgenic animal, but which is inserted into the animal's genome at a location which differs from that of the natural gene.

"Embryonal cells" as used herein include embryonic stem (ES) cells and fertilized oocytes. In the case of fertilized oocytes, the preferred method of transgene introduction is by microinjection, whereas for ES cells, the preferred method is electroporation. However, other methods including viral delivery systems such as retroviral infection, or liposomal fusion can be used.

By the term "operably linked" as used herein is meant that the DNA encoding the enhancer is in proximity with the gene encoding the transgene to allow transcriptional regulation of the transgene.

By "functionally active" is meant possessing any in vivo or in vitro immunological activity which is characteristic of a mature wild-type natural killer cell or T lymphocytes.

By "biologically active" is meant a protein or peptide which possesses any in vivo or in vitro activity which is characteristic of the naturally occurring human or mouse CD3-ε protein.

By "enhancer" is meant a cis-acting nucleic acid element which controls transcription initiation from homologous as well as heterologous promoters independent of distance and orientation. Preferably, an enhancer also controls the tissue and temporal specificity of transcription initiation.

"Homologous", as used herein in reference to DNA molecules, refers to the nucleotide sequence similarity between two DNA molecules. When a nucleotide position in both of the DNA molecules is occupied by the same nucleotide, then they are homologous at that position. Thus, by "substantially homologous" is meant a nucleotide sequence that is largely but not wholly homologous, and which retains the same functional activity as the sequence to which it is homologous.

Unless defined otherwise, all technical terms and scientific terms used herein have the same meaning as commonly understood by one of ordinary skill in the art to which this invention belongs. Although any methods and materials similar or equivalent to those described herein can be used in the practice or testing of the present invention, the preferred methods and materials will now be described. All publications mentioned hereunder are incorporated by reference. In addition, the materials, methods and examples are illustrative only and not intended to be limiting.

The transgenic non-human mammals of the invention which are substantially deficient in T lymphocytes and natural killer cells, or substantially deficient in T lymphocytes, natural killer cells and B lymphocytes are particularly useful as models for the role of human cells of the immune system in immune diseases, tumorigenesis, and transplant rejection.

Other features and advantages of the invention will be apparent from the following detailed description, and from the claims.

DETAILED DESCRIPTION

First the drawings will be briefly described.
Drawings FIG. 1A is a diagram of the DNA constructs used to make the CD3-ε transgenic mice. The exons and the 3' enhancers regions are indicated. The dotted lines from pL12 to pL12Δ1 and pL12Δ2 indicate the deleted regions. The circles in pL15, pL16 and pL19 indicate the joining points between mouse and human sequences. The wild type mouse CD3-ε gene ($CD3ε_M$) is also shown for comparison.

FIG. 1B is a schematic diagram of the predicted protein structures expressed by the transgenes of FIG. 1A on the cell surface.

FIG. 1C is a comparison of the mature human and mouse CD3-ε amino acid sequences. The starting point of each exon is indicated by an arrow. Homologies are indicated by grey boxes, and the signal transduction motif by a white box.

Figure 3A:
Figure 3C:
Figure 3B:
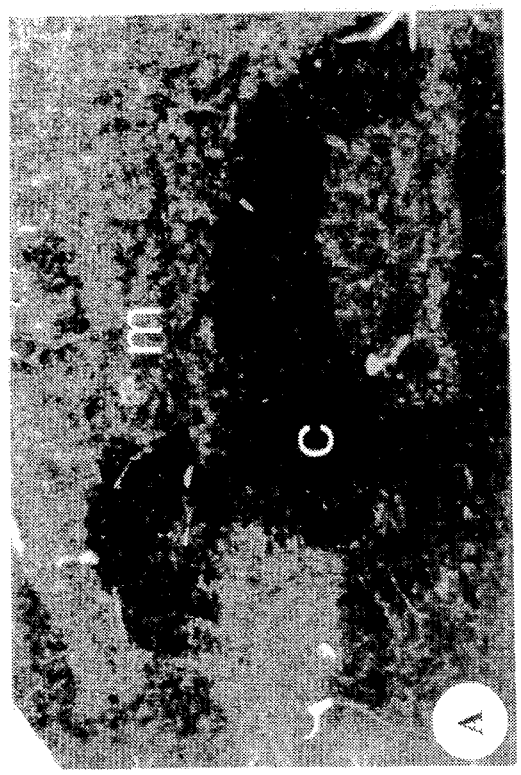
Figure 3D:
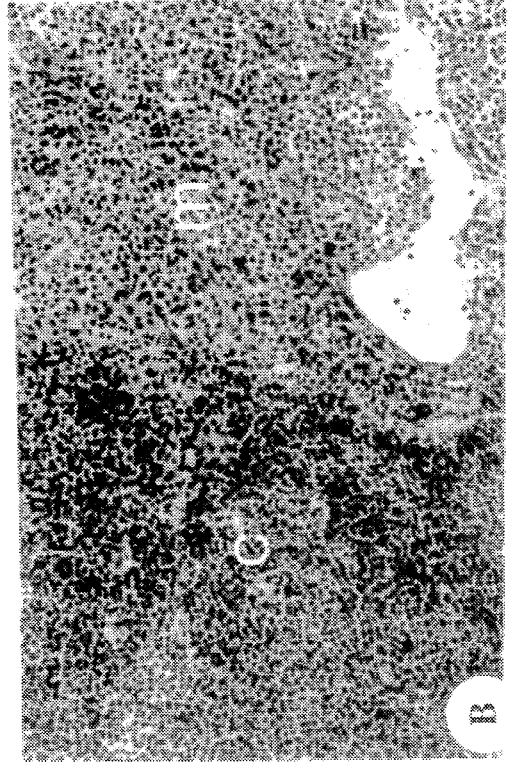
Figure 3E:
Figure 3G:
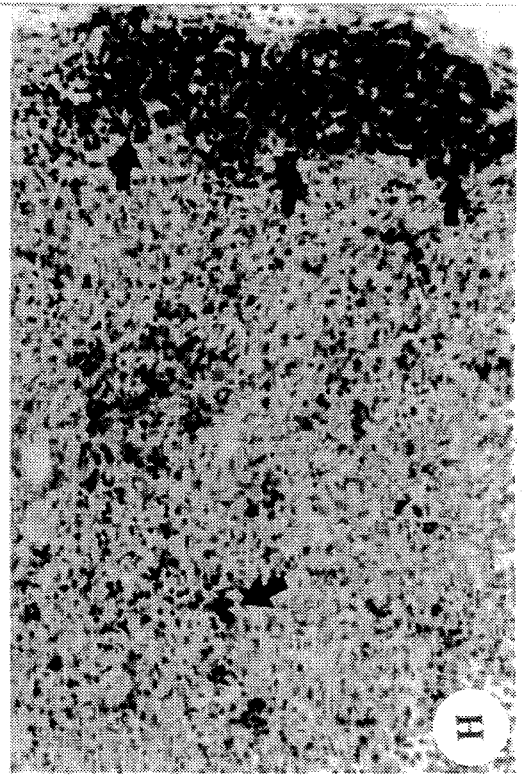
Figure 3F:
Figure 3H:
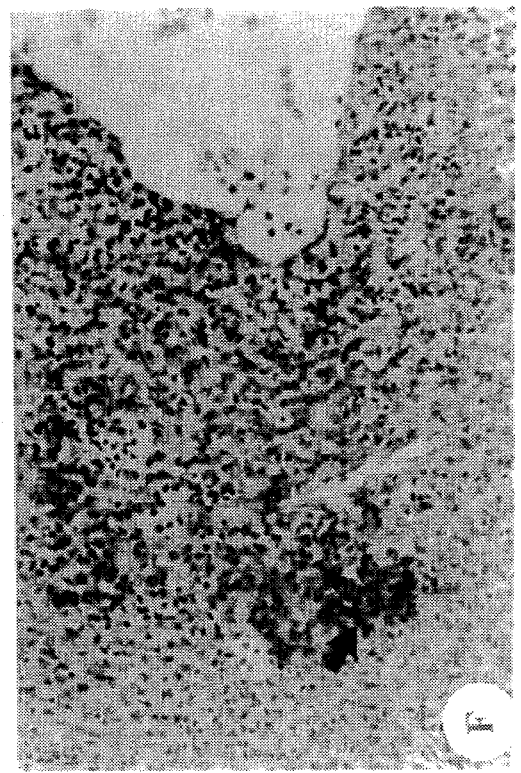
Figure 3I:
Figure 3J:
Figure 3K:
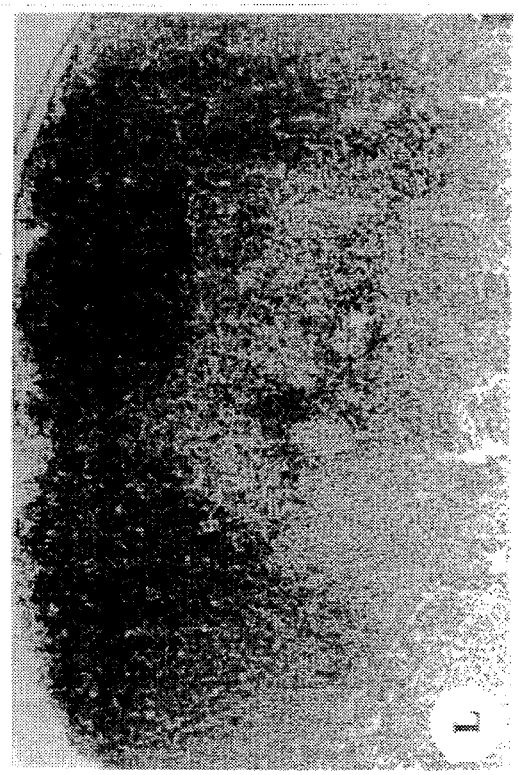
Figure 3L:
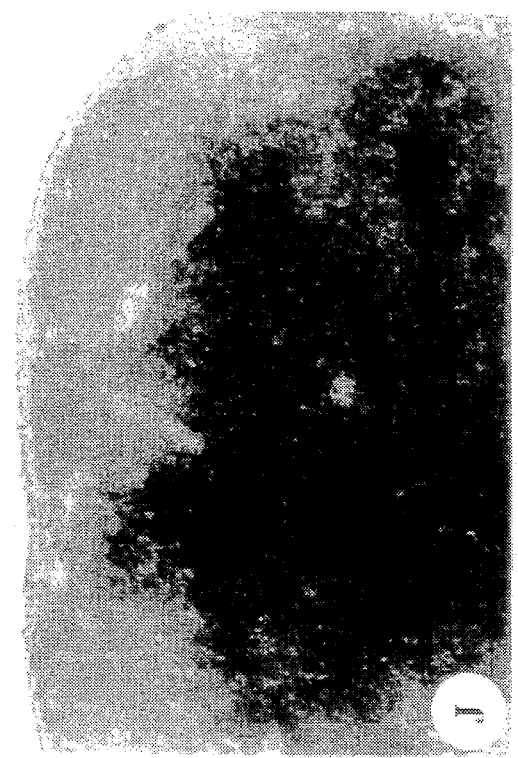
Figure 3M:
Figure 3O:
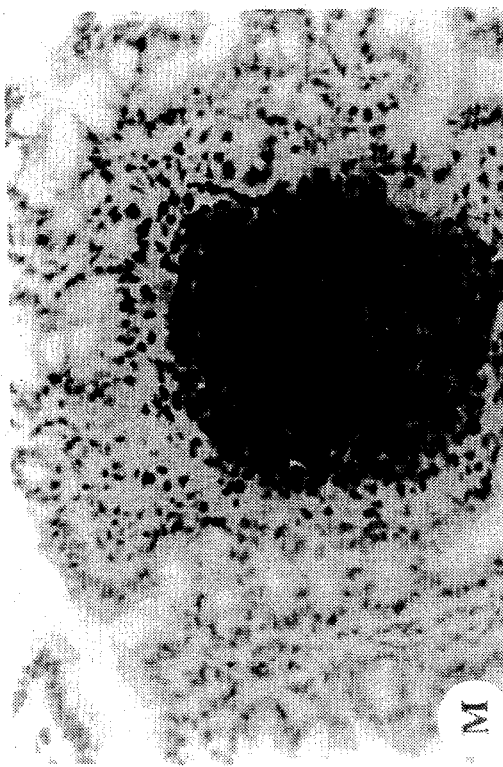
Figure 3N:
Figure 3P:
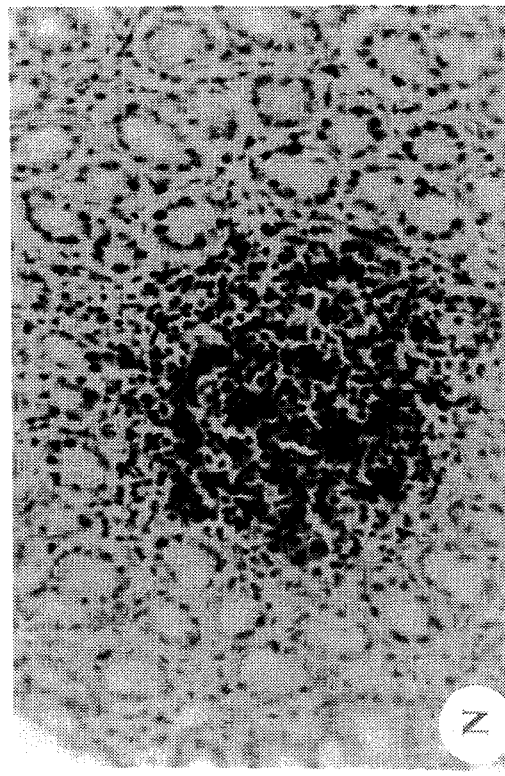

FIGS. 3A–3P are photographs which show the histology of thymus, lymph nodes, and Payer's patch in the homozygous pL12 line 26 mice. Frozen sections from 8 weeks old transgenic and wild type mice were used for following staining: A–D: Hematoxylin and eosin staining of wild type thymus (A, magnifications: 25x; B, 160x) and transgenic thymus (C, 25x; D, 160x). The medulla (m) and cortical (c) in the wild type thymus are indicated. (Note there are two large cysts in the transgenic thymus (C). E–F: Thy-1 staining of transgenic thymus (E, 25x; F, 160x). Only few patches of cells were positive for Thy-1 (e.g., cells indicated by arrows). G–H: B220 staining of transgenic thymus (G,25x; H, 160x). I–L: Hematoxylin and eosin (I,J) and Thy-1 (K,L) staining of a wild type (I and K, 63x) and a transgenic lymph node (J and L, 63x). No Thy-1$^+$ cells were detected in the transgenic lymph node, and cell density in a normal T cell area was lower than that in control lymph nodes. M–P: Thy-1 staining (M,N) and B220 staining (O,P) of a wild type (M and O, 250x) and a transgenic Payer's patch (N and P, 250x). No Thy-1+ cells were detected in the transgenic Payer's patch, but the numbers of B220+ cells was increased.

Figure 4:
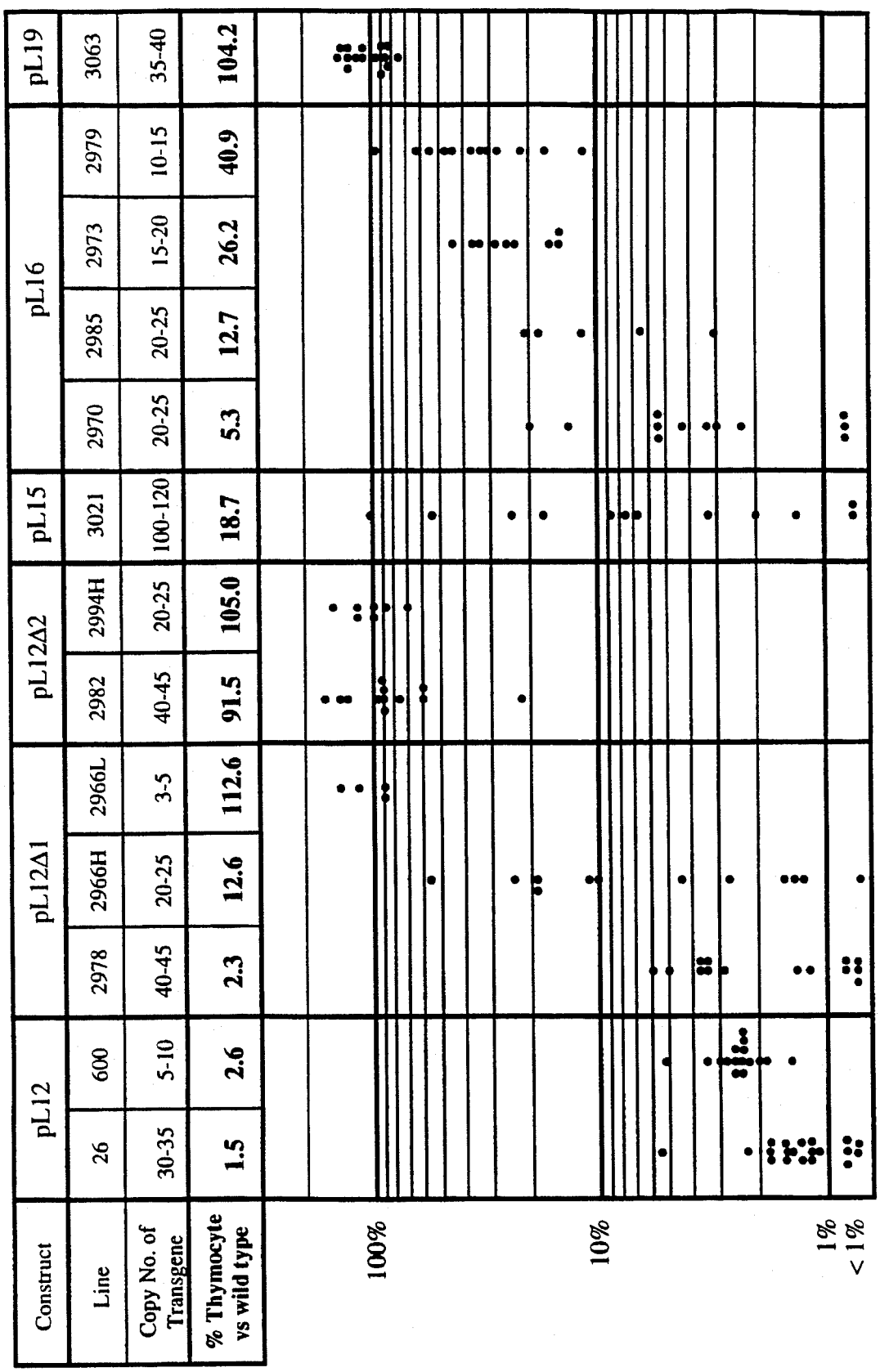

FIG. 4 is a representation of the total number of thymocytes per thymus in homozygous transgenic mice. The numbers are shown in comparison to wild type litter mates in a logarithmic scale. Data were obtained from mice ranging from newborn to 6 months old. At least one, or two or more, wild type litter mates were analysed in parallel with transgenic mice. The average number of total thymocytes from the wild-type litter mates was used as 100%, and the number of total thymocytes from each transgenic mouse was converted into a relative percentage. For new-born mice, the number of total thymocytes from each mouse was collected, and the conversion was done after determination of the phenotype by Southern blots. Each dot represents a relative cell number from one homozygous mouse.

Figure 5:
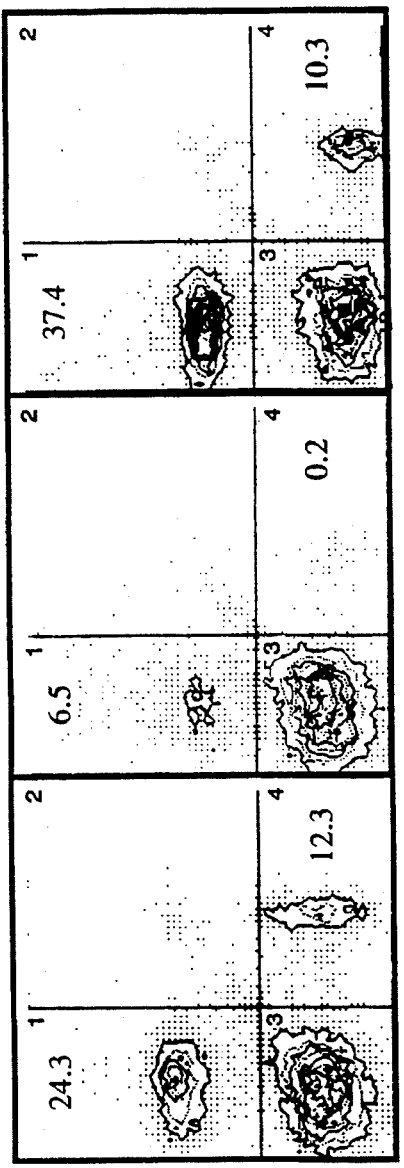
Figure 5:
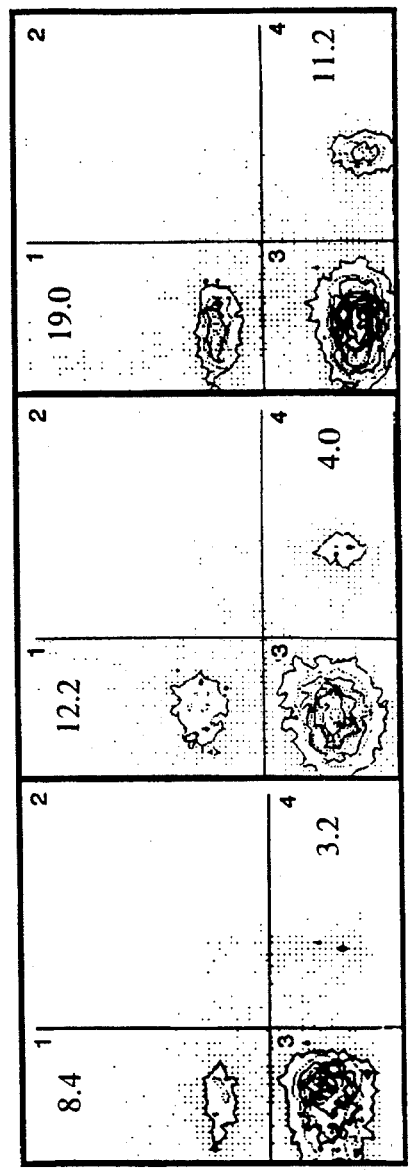

FIG. 5 depicts FACS analysis of CD4 and CD8 surface expression of spleen cells from wild type and homozygous transgenic mice. The transgenic lines are indicated.

Figure 6A:
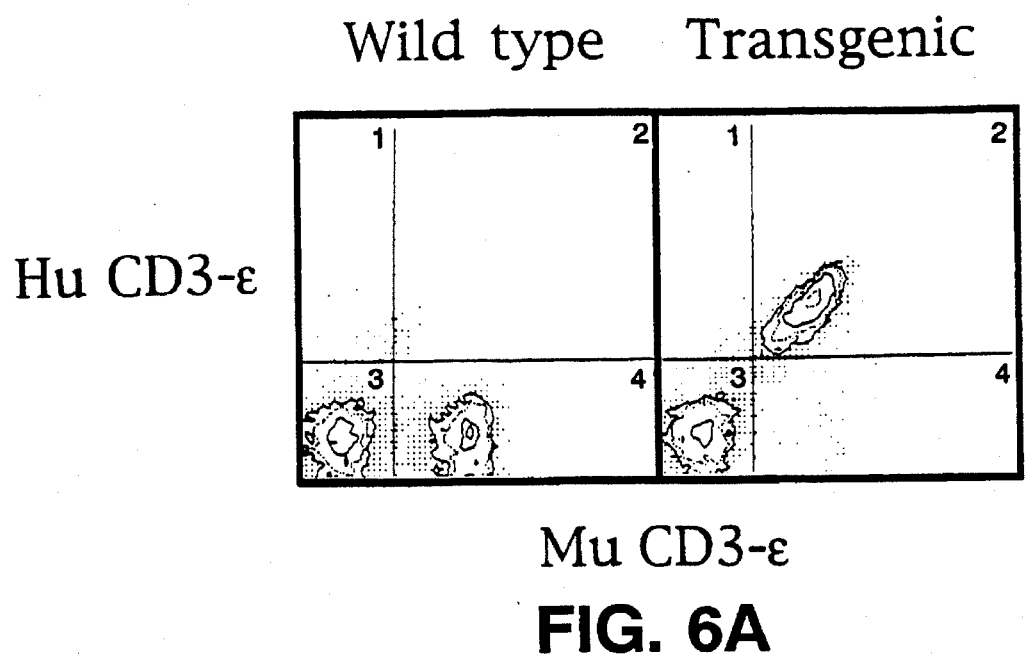

FIG. 6A depicts a flow cytometric analysis of the surface expression of the mouse CD3-ε and the human CD3-ε proteins in spleen cells from wild type and heterozygous pL12 line 600 mice. T cells from the transgenic spleen are double positive for both the mouse and human CD3-ε proteins.

Figure 6B:
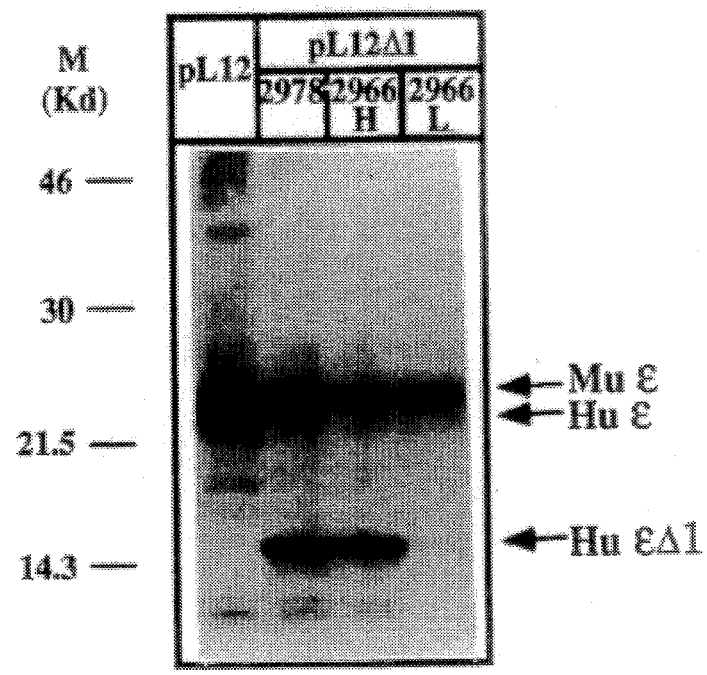

FIG. 6B represents a Western blot analysis of transgene expression in the spleen cells from pL12 line 600 and pL12Δ1 lines 2878 (40–45 copies/cell), 2966H (20–25 copies) and 2966L (3–5 copies).

Figure 7C:
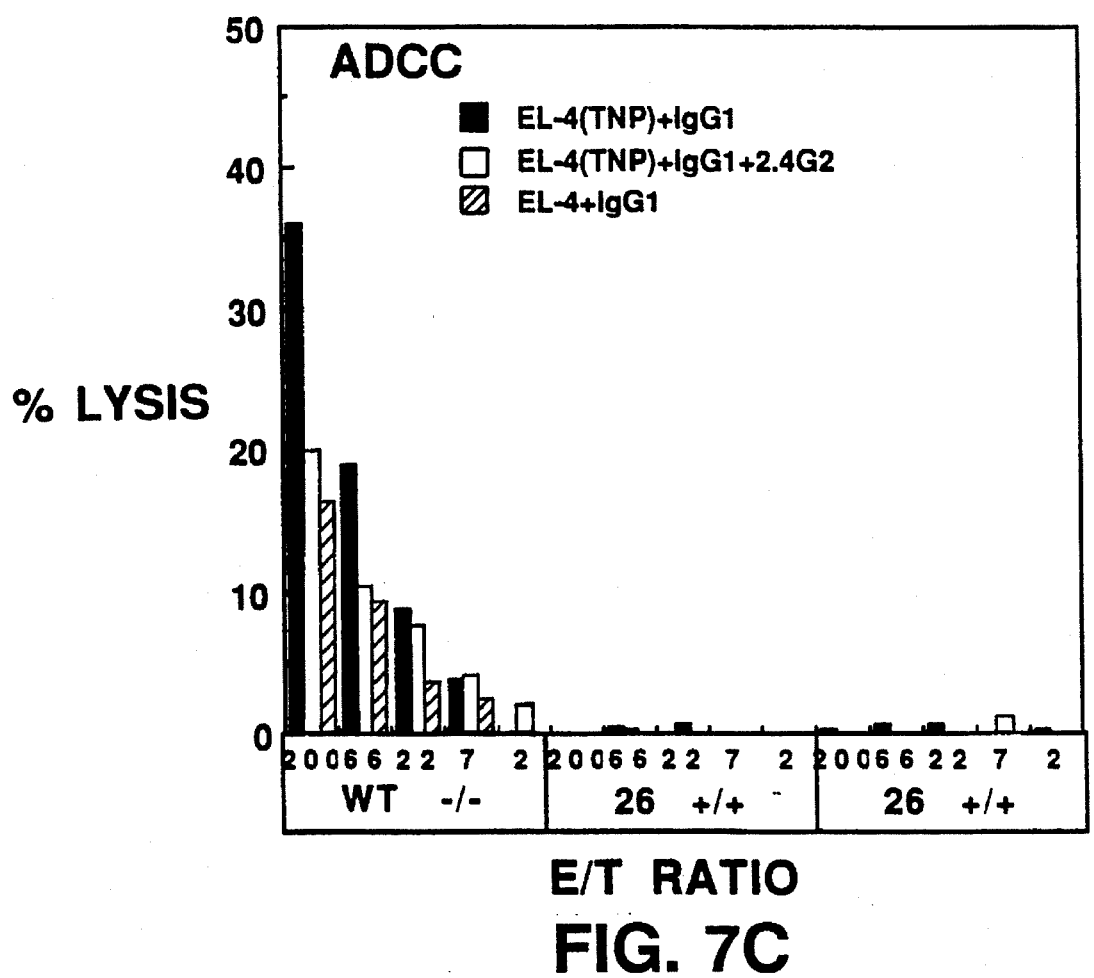
Figure 7A:
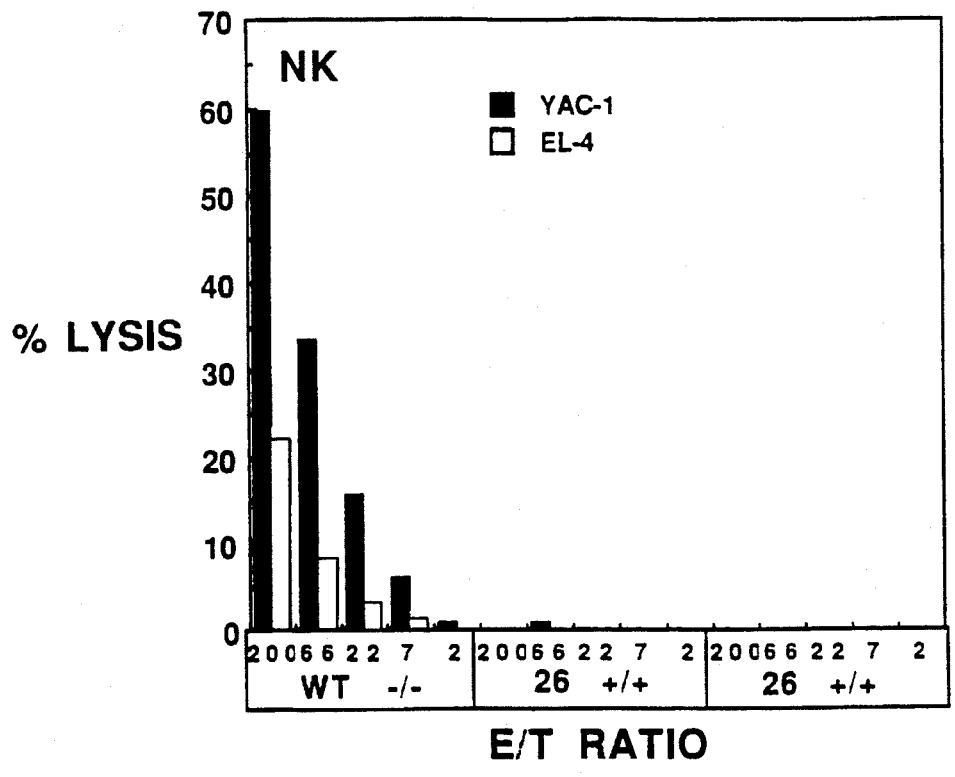
Figure 7B:
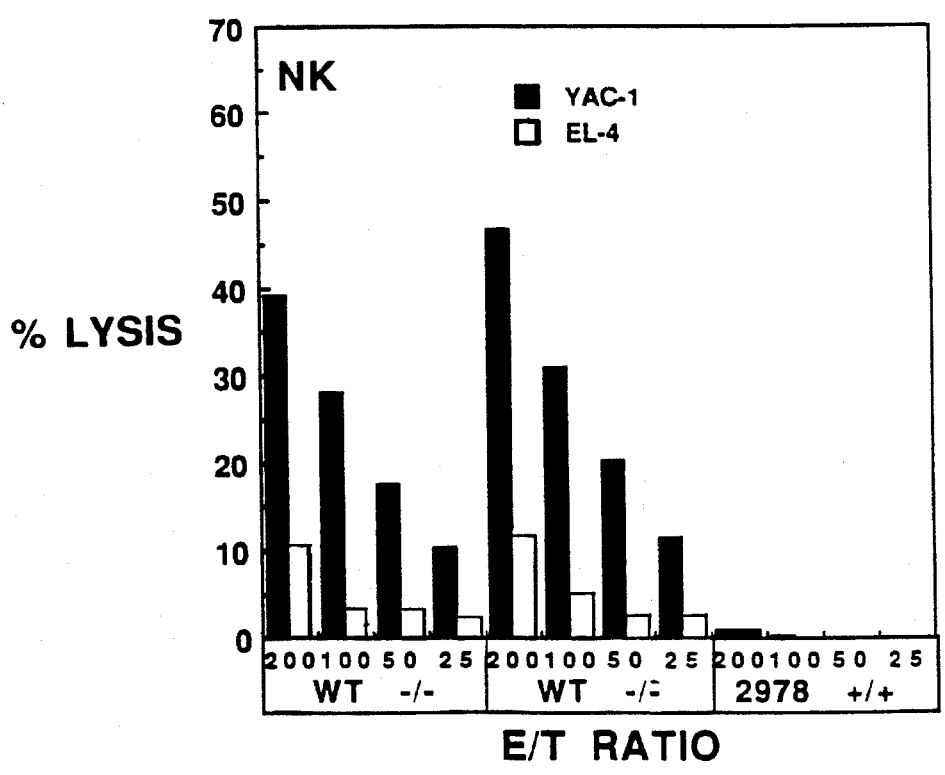

FIG. 7A depicts the results of a NK cell activity assay for spleen cells from poly I:C treated homozygous pL12 line 26 and wild type mice against YAC-1 and EL-4 target cells. FIG. 7B depicts the results of a NK cell activity assays of line pL12Δ1-2978 and wild type mice against YAC-1 and EL-4 target cells. FIG. 7C depicts the results of ADCC assay.

Figure 8A:
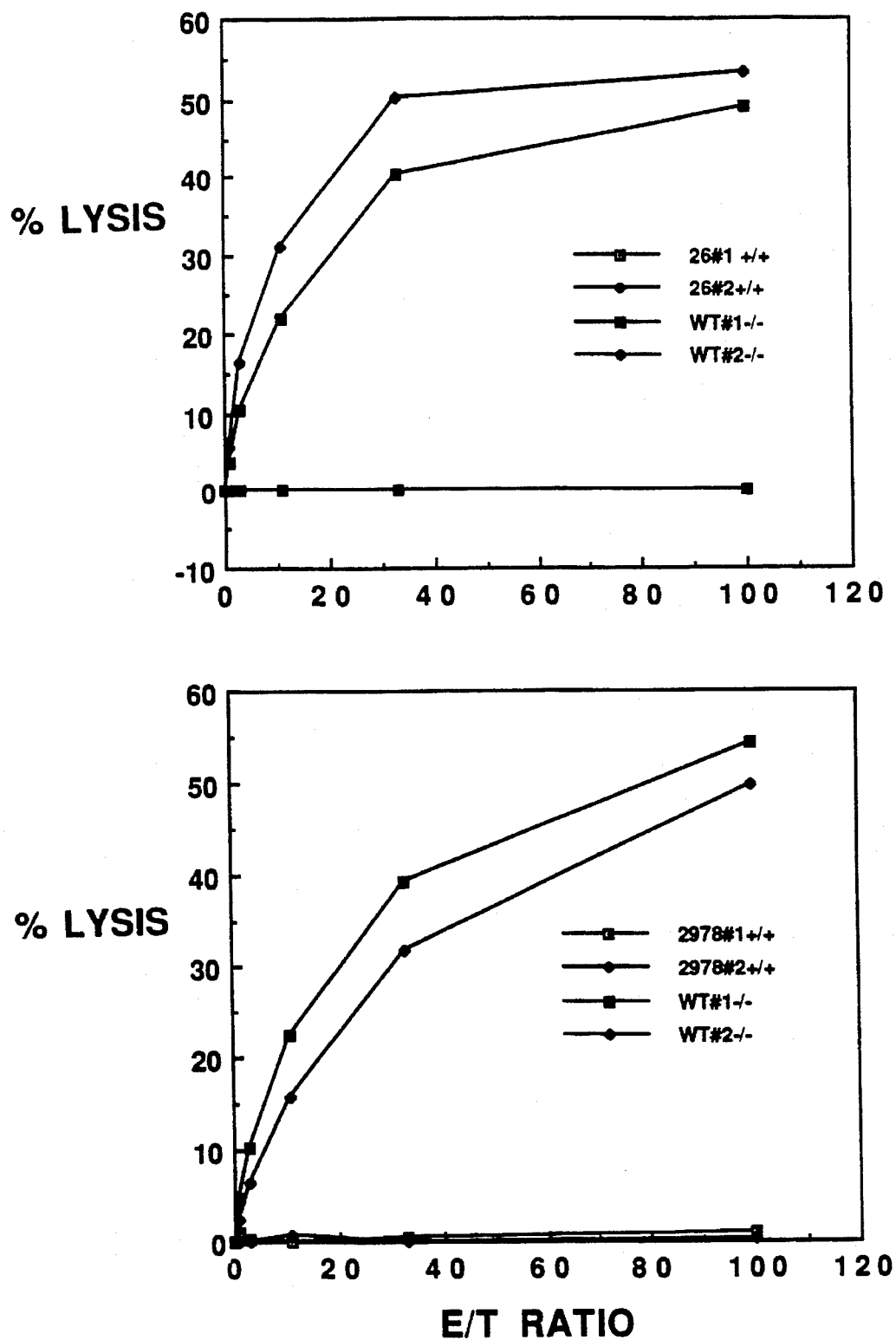
Figure 8B:
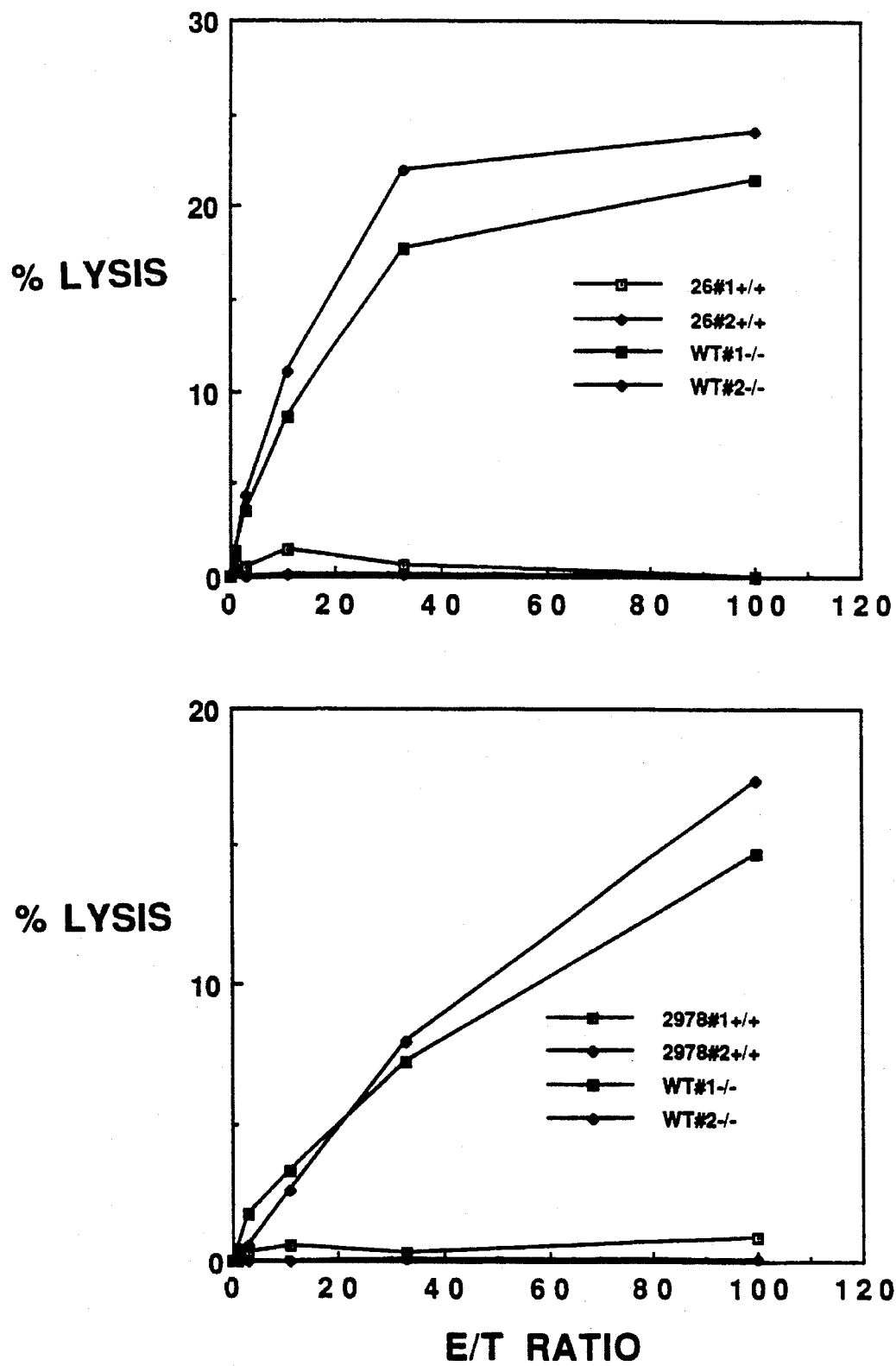
Figure 8C:
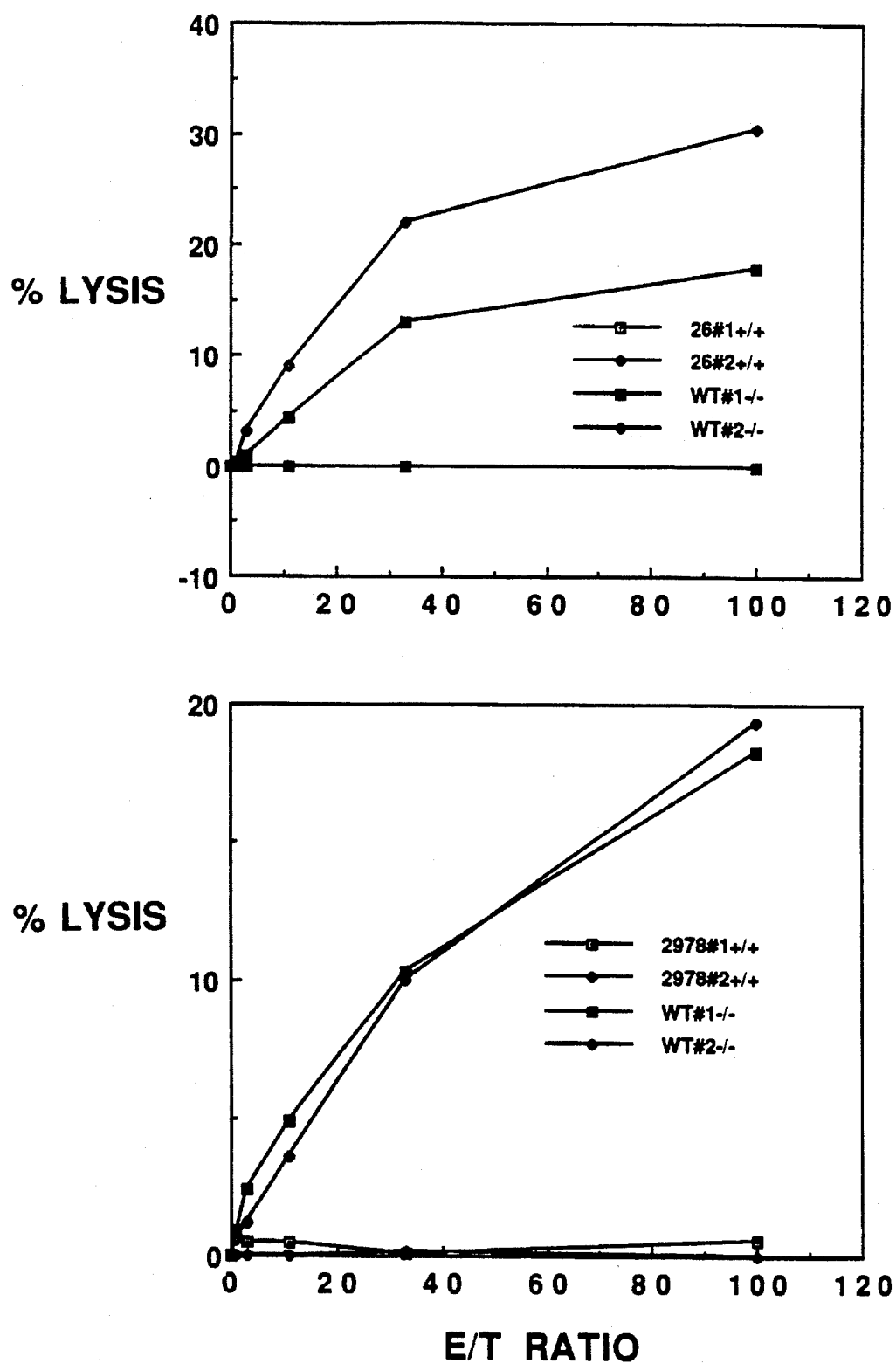

FIGS. 8A–8C depicts the results of NK cell activity assay for spleen cells from LCMV treated homozygous pL12 line 26 and pL12Δ1 line 2978 mice. (A) cytoxicity of line 26 (top) and line 2978 mice (bottom) as well as wild type control mice against YAC-1 target cells. (Note that each of the two line 26 mice had 0% lysis and showed on the same line). (B) same as (A) except that L-929 cells were used as target cells. (C) same as A except that MC57G cells were used as target cells.

Figure 9:
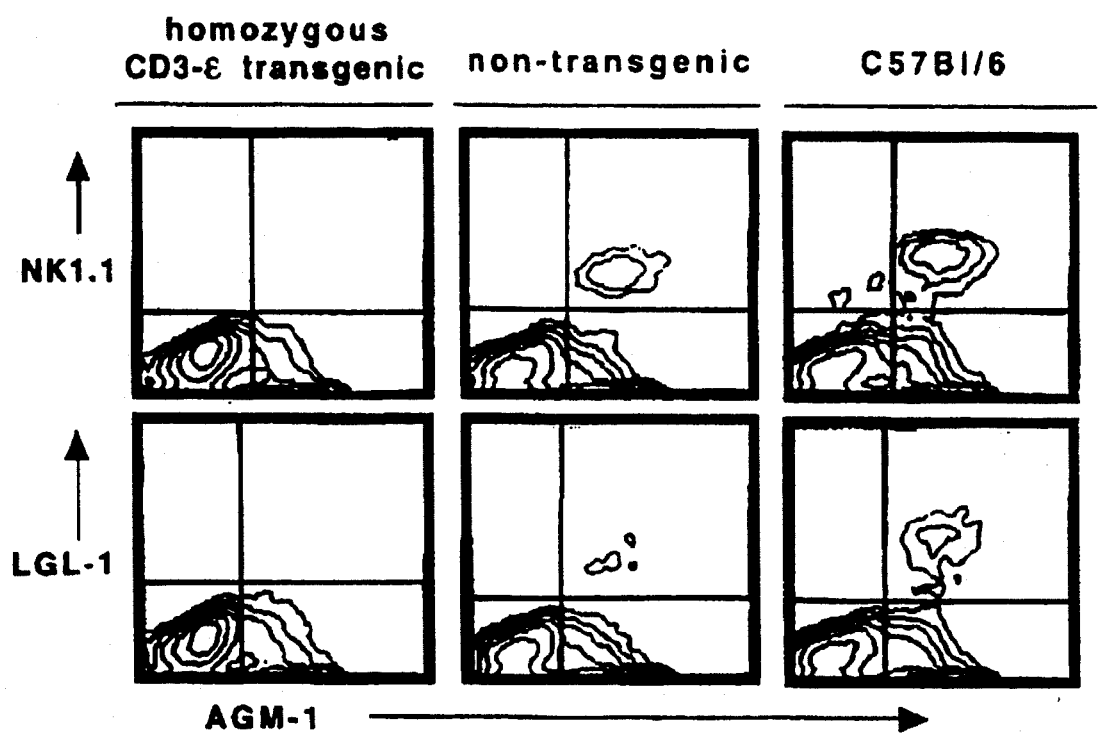

FIG. 9 depicts a cytometric analysis for AGM1 and NK1.1 (top) or AGM1 and LGL-1 (bottom) expression in sIg⁻ spleen cells from homozygous pL12 line 26 and wild type litter mates (non-transgenic) as well as C57BL/6 mice.

Figure 10:
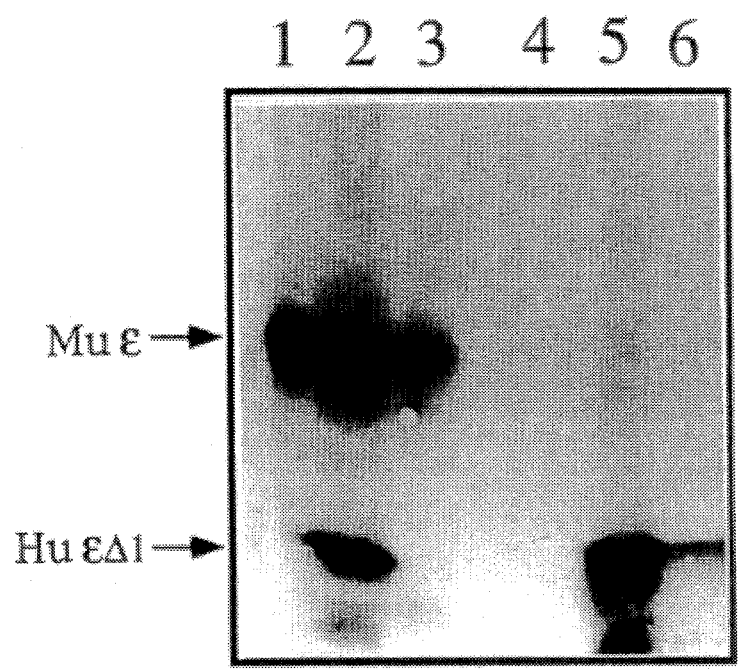

FIG. 10 represents a Western blot analysis of CD3-ε expression in the mouse NK cells. Lane 1: EL-4 cells; Lane 2, spleen cells from a heterozygous pL12Δ1-2978 mouse; lane 3: LAK cells from C57BL/6 mice; Lane 4 NK-enriched spleen cells from non-transgenic litter mates; Lane 5: NK-enriched spleen cells from a heterozygous pL12Δ1-2978 mouse; Lane 6; T-\B-cells from a anti-AGM1 treated heterozygous pL12Δ1-2978 mouse.

Figure 11:
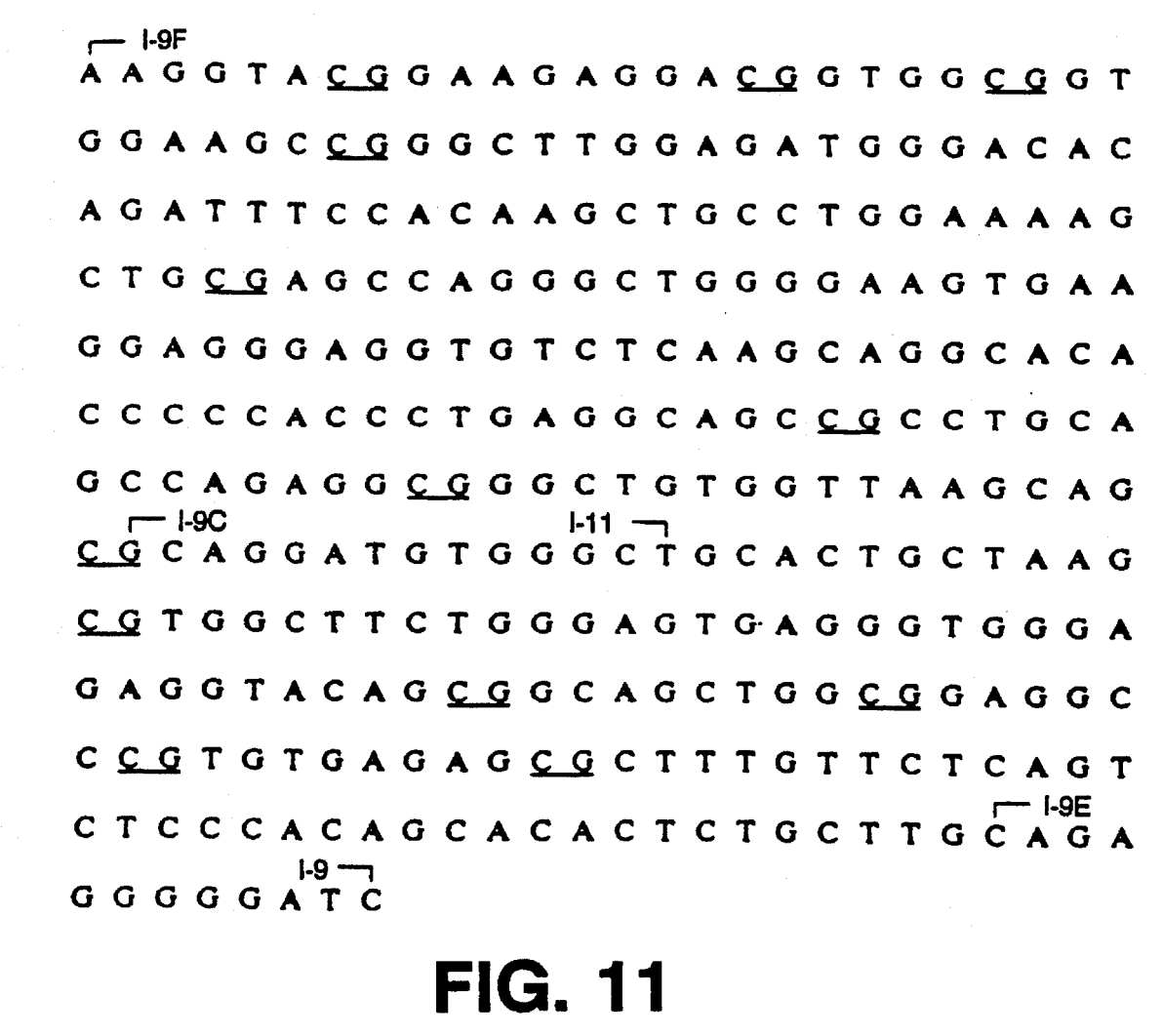

FIG. 11 is the nucleotide sequence of the E2 and E1 of the human CD3-ε enhancer (SEQ ID NO: 1). Domain E2 is defined as the region between the 5' boundaries of pI-9F and pI-9C; domain E1 is defined by the sequence from the 5' boundary of pI-9C to the 3' end.

Construction of DNA Molecules

The human genomic CD3-ε gene and flanking sequences were reconstructed from two overlapping bacteriophage inserts using the unique XhoI site in the center of the gene. The resultant plasmid, pL12 (Clevers et al., *Proc. Natl. Acad. Sci.* 85: 8156, 1989), includes a 24 kb SmaI-SalI fragment which contains the promoter, coding and enhancer sequences of the human CD3-ε gene (GenBank Accession No. x03884; Gold et al., Nature 321: 431, 1986).

pL12Δ1 was constructed by deleting a 0.6 kb fragment containing exons 4A–5 from pL12 by partial digestion with BglII, followed by isolation and religation of the large fragment which lacked the 0.6 kb BglII-BglII fragment using standard methods (e.g., see Sambrook et al., *Molecular Cloning: A Laboratory Manual*, 2d ed., Cold Spring Harbor Press, 1989, hereby incorporated by reference). A further deletion of the 1 kb BglII-BglII fragment containing exon 6 produced pL12Δ2.

pL15 was made by ligation of a 13 kb NotI-BglII fragment containing the promoter and exons 1 through 5 of the mouse CD3 gene to a 10 kb NotI-BglII fragment containing exon 6 through 3.5 kb of the 3' untranslated region of the human CD3 gene as well as 3 kb of the vector pGEM4 (Promega). The 13 kb fragment of the mouse CD3-ε (GenBank Accession No: J02990; Gold et al., Proc. Natl. Acad. Sci. 84: 7649, 1987) gene which was subcloned into SK+ vector (Stratagene) was isolated by complete digestion with NotI coupled with partial digestion with BglII. The 10 kb fragment of the human CD3 gene was isolated by similar digestion of pL12 DNA.

pL16 was constructed by ligation of a 13.5 kb EcoRI-XbaI fragment containing the promoter and exons 1 through 6 of the mouse CD3 gene, to a 9 kb EcoRI-XbaI fragment containing exon 6 through 3.5 kb of the 3' untranslated region as well as 3 kb of vector sequences.

pL19 was constructed by ligation of a 16.5 kb SalI-HindIII fragment including 3 kb of vector at 5' end connected to human CD3 gene from the promoter through exon 4, to a 11.5 kb HindIII-SalI fragment containing the mouse CD3 gene from exon 5 through 5.5 kb 3' untranslated region.

All of the DNA constructs above were confirmed by intensive restriction enzyme mapping, and by Southern analyses using probes derived from different locations of the human and mouse sequences.

Generation of Transgenic Mice

C57BL/6J and CBA/J mice were purchased from Jackson Laboratory (Bar Harbor, Me.). The entire insert from each construct was isolated from vector sequences by digestion with NotI and SalI, followed by gel electrophoresis and CsCl centrifugation. Each purified insert was microinjected into (C57BL/6J×CBA/J) F2 embryos to generate transgenic founders as described by Hogan et al. (Manipulating the mouse embryo: A laboratory manual, CSH Press, Cold Spring Harbor, N.Y., 1986) Founder animals were bred with (C57BL/6J×CBA/J) F1 to establish independent lines, and sibling matings were performed to obtain homozygous lines. All the mice were maintained in micro-isolator cages with autoclaved food, water, and beddings according to the standard general guidelines for immunodeficient animals (National Research Council, 1989, Chapter 4 in "Immunodeficient Rodents, A guide to This Immunobiology, Husbandry, and Use, National Academy Press).

Screening of Mice

Genomic DNA was isolated from mouse tails and subjected to Southern blot analysis by standard methods. Briefly, 5 to 10 ug genomic tail DNA was digested with HindIII or EcoRI, separated on a 0.8% agarose gel, and transferred to a nylon membrane (Millipore) under vacuum transfer (Pharmacia) according to the manufacturer's instructions. The DNA was then fixed on the membrane with a UV cross-linker (Stratagene), and hybridized with the probe or probes labelled with [α-32P]dCTP by random hexamer method (Feinberg et al., Anal. Chem. 132: 1983) in a hybridization solution (7%SDS, 0.25M $Na_2PO_4$, pH7.4) at 65° C. overnight in a rotating hybridization incubator (Robbins Scientific, La Jolla). The final wash was carried out in 0.2× SSC, 0.5% SDS, 65° C., 30 min. The blots were then exposed to X-Ray film overnight at −80° C.

Mice containing the transgenic DNA constructs were identified with a 1.4 kb human CD3-ε cDNA probe, with the exception of pL19 mice which were identified using a 0.8 kb genomic DNA containing the human CD3-ε exon 4 as the probe. The copy number of the transgene was determined by using construct DNA as a control. To determine homozygosity, the Southern blots were either co-hybridized, or hybridized subsequently, with a 1.5 kb mouse CD3-ε cDNA probe to identify the mouse CD3-ε genomic DNA, which was also used as a quantitative DNA control.

Western Blot Analysis

Western analyses were performed as previously described (Sancho et al., J. Immunol. 148: 1315, 1992). Briefly, cells were lysed in NP40 buffer (1% Nonidet-40, 150 mM NaCl, 0.14% Trothanolamine, 1 mM EDTA, 10.8 mM Iodoacetamide, 1 mM PMSF, and 1 μg/ml each of leupeptin, pepstatin and antipain), separated by 15% SDS-PAGE, transferred onto PH79 membrane (Schleicher & Scheull) using a semidry transfer system (Pharmacia), and stained with an anti-CD3-ε polyclonal antibody (DAKO). To detect small peptide (pL12Δ2), a three layer gel system was used (Schagger et al., Anal. Biochem. 166: 368, 1987).

Flow Cytometric Analysis

Single cell suspensions from thymus, spleen, and lymph nodes and gut from 6–12 week old mice were prepared by standard procedures (e.g., see Current Protocols in Immunology, Coligan et al., eds, John Niley & Sons, Chap. 3). Approximately 5×10⁵ cells were preincubated in 96-well round bottom dishes (Costar) for 20 min in 100 µl of staining solution (phosphate buffered saline, pH 7.2, 0.05% sodium azide, and 2.5% fetal calf serum) and 10 µl each of normal mouse, hamster and rat sera (Jackson ImmunoResearch). The cells were then stained for 30 to 60 min by addition of 100 µl staining solution containing 0.5 µg of antibodies conjugated with either fluorescein isothiocyanate (FITC) or phycoerythrin (PE). The cells were washed three times in PBS, 0.05% sodium azide, and fixed in PBS, 0.05% sodium azide, 1% formaldehyde. Cells were kept on ice during the staining procedures, and kept at 4° C. until analysis. Flow cytometric analyses were carried out with a FACSstar$^{plus}$ (Becton Dickinson) using FACScan software. The antibodies used in this study were: 2C11 (Mouse CD3-ε), HIT-3A (Human CD3-ε), H57-597 (TCR-αβ), GL-3 (TCR-γδ), RM4-5 (CD4), 53-5.8 (CD8α), 53-2.1 (Thy1.2), M1/69 (HSA), 53-7.3 (CD5), 7D4 (IL2-Rα), M1/70 (Mac-1), RB6-8C5 (Gr-1), RA3-6B2 (B220), 2.4G2 (FcγII), PK136 (NK1.1) which were purchased from Phar Mingen. Anti-AGM-1 antibody was purchased from WAKO (Tex.) anti-IgM antibody was obtained from Jackson Immunoresearch (West Grove, Pa.), and anti-LGL-1 antibody was a gift from Dr. John Ortaldo (NCI).

Histology

Lymphoid organs were frozen at −20° C. and mounted for cryostat sectioning. Sections 5 µm thick were fixed in 4% paraformaldehyde, PBS (pH 7.4) at 4° C. for 8 min and treated with 0.6% $H_2O_2$ in methanol for 10 min. The sections were stained with hematoxylin and eosin, or used for immunohistochemistry as described below. The sections were blocked with 2% normal rat serum, PBS (pH 7.40 for 20 min, stained with biotinylated primary antibodies for 1 hr, followed by ABC reagent (Vector Labs, Burlington, Calif.) for 45 min. The sections were counterstained with hematoxylin, dehydrated, and mounted. Biotinylated rat anti-mouse Thy 1.2 and B220 antibodies were purchased from PharMingen.

Cytotoxicity Assays

NK-mediated cytotoxic lysis was determined by a standard 4 hour $^{51}$Cr release assay as described (Biron et al., J. Immunol. 139: 1704, 1987). ADCC was performed as described (Rodewald et al., Cell 69: 139, 1992) except that 3 mM 2,4,6-trinitrobenzene sulfonic acid was used instead of 30 mM.

Enrichment of NK Cells

NK cells were negatively selected by incubation of spleen cells with anti-CD3 (145-2C11) and anti-IgM antibodies plus complement as described (Coligan et al., 1991, supra). Depletion in vivo of NK cells was achieved by injection of anti-AGM1 antibody into mice two days before harvesting of spleen cells. Lymphokine activated killer (LAK) cells was made by cultured spleen cells with 1000 units/ml IL-2 (Cetus) for 6 days (Grimm et al, J. Exp. Med. 158: 1356, 1983).

T Cell Development is Abrogated in Transgenic Mice Containing the Human CD3-ε Gene Transgenic mice were generated using a 24 kb genomic DNA fragment, pL12, which contained the entire human CD3-ε gene including 12 kb of the coding portion, 8.5 kb of 5' upstream sequences and 3.5 kb of 3' downstream sequences (FIG. 1A). Two stable transgenic lines were derived from two founder mice bearing high copy number of the transgene: line 26 (30–35 copies/genome) and line 600 (5–10 copies/genome).

Histological analyses indicated that the thymuses of newborn homozygous line 26 mice were extremely small or undetectable, and only minute thymic remnants could be seen in the adult mice. These analyses further revealed that, while a normal thymus has a cortical layer that is packed with immature thymocytes and a medulla that is packed with mature T cells, the homozygous thymus remnants had a clasped thymic structure which lacked a clear distinction between the cortical layer and medulla. The homozygous thymus consisted primarily of stroma cells, and the lymphocyte density was even lower than that in the wild type medulla (FIGS. 3C–D). Whereas Thy-1 staining in a wild type thymus was very heavy in the cortical and modest in the medulla (not shown), there were only small clusters of Thy-1 positive cells in the homozygous thymus (FIGS. 3E–F).

Figure 2B:
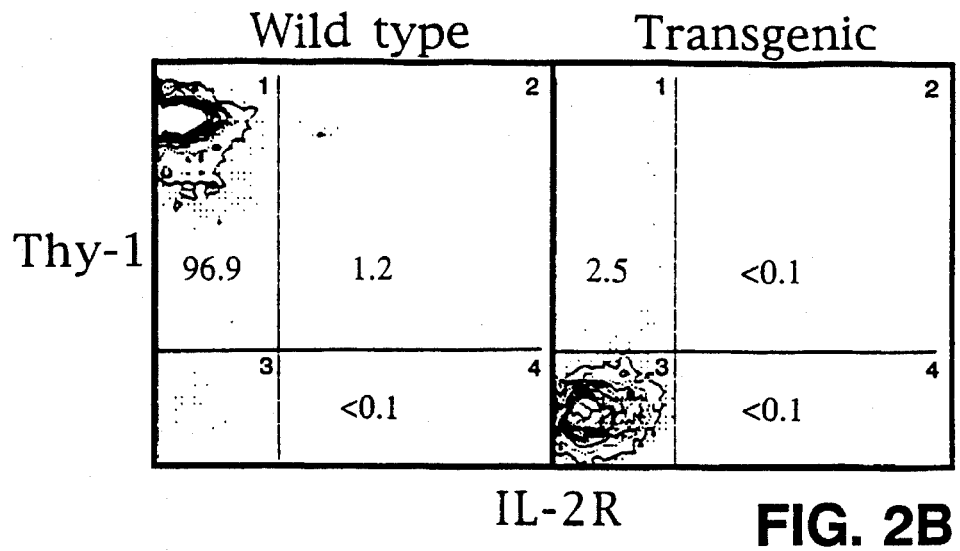
FIG. 2B depicts a flow cytometric analysis of thymocytes which were double stained with Thy-1 and IL-2R. No IL-2R$^+$ cells were detected in the transgenic thymus.
Figure 2C:
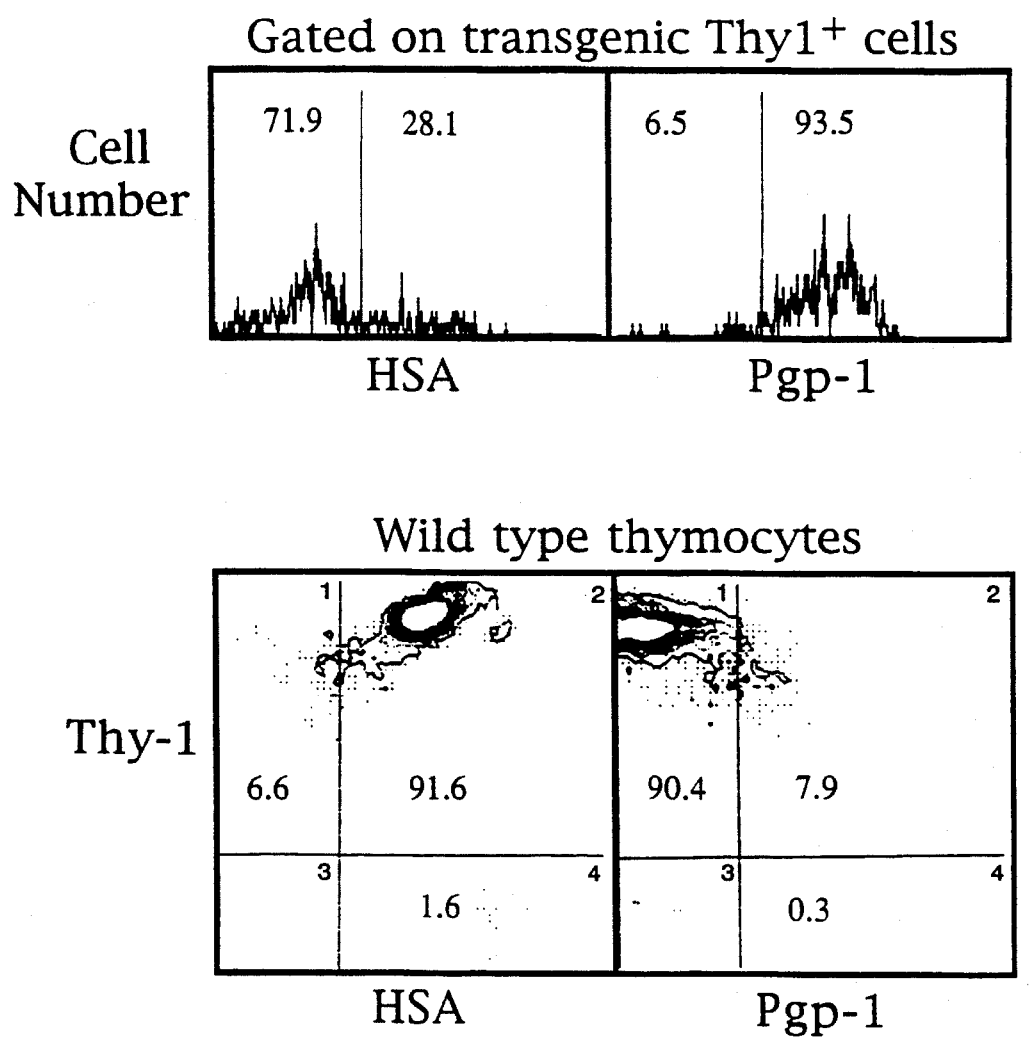
FIG. 2C depicts a flow cytometric analysis of Thy1$^+$ cells from FIG. 2B thymocytes which were stained with HSA and Pgp-1. These cells were all Pgp-1 positive and mostly HSA$^-$.
Figure 2A:
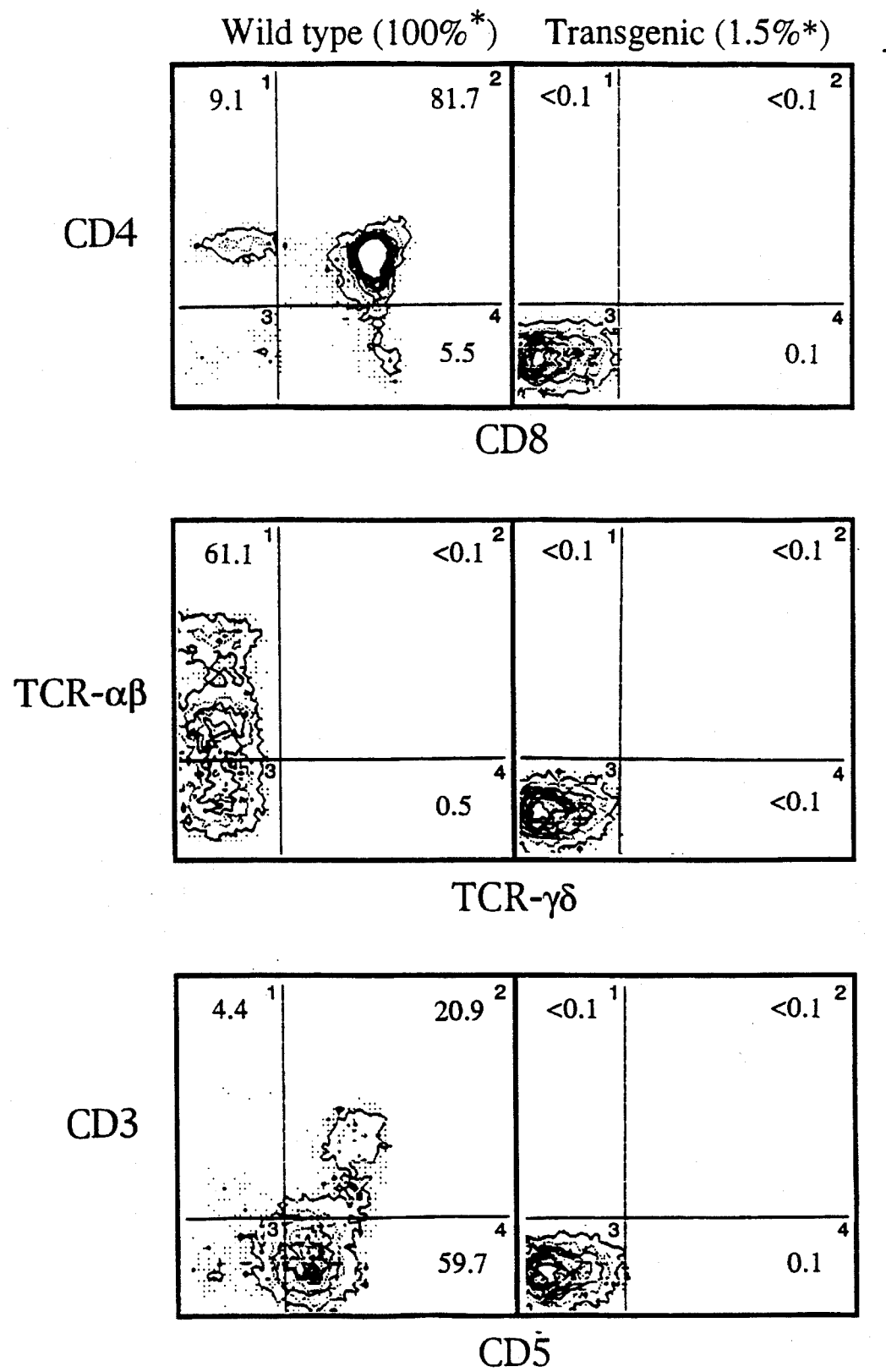
FIG. 2A depicts a flow cytometric analysis of thymocytes and spleen cells from 6 to 8 weeks old homozygous line 26 transgenic mice and wild type control mice which were double stained with following fluorescent antibodies: CD4 and CD8 (top), TCR-αβ and TCR-γδ (middle), CD3 and CD5 (bottom) [*: % of total thymocytes/thymus in transgenic mice versus that in wild type litter mates.].

Total number of thymocytes in homozygous transgenic mice ranging from newborn to six months old was found to be reduced to an average of 70-fold less than in their wild type litter mates (FIG. 4). We determined the phenotypes of the remaining thymocytes, and found that they were $CD4^-$ $CD8^-$, $CD3^-CD5^-$, and TCR-αβ$^-$/TCR-γδ$^-$, indicating an absence of detectable levels of mature T cells (FIG. 2A). We also found that the majority of the remaining cells were Thy1$^-$ IL2Ra$^-$ (FIG. 2B). When the small population of Thy1$^+$ cells was further analyzed, it was determined that they are all Pgp-1$^+$ and mostly HSA$^-$, in contrast with wild type thymocytes which are mostly Thy1$^+$/Pgp-1$^-$/HSA$^+$ (FIG. 2C). Since immature double negative (DP) T cells most likely arise from early precursor "null cells" through sequential differentiation from Thy1$^-$IL-2Ra$^-$ HSA$^-$Pgp-1$^+$ cells to Thy1$^+$IL-2Ra$^+$HSA$^+$Pgp-1$^+$ cells, and then to Thy1$^+$ IL-2Ra$^-$ HSA$^+$Pgp-1$^-$ cells, (Scollay et al. Immunol. Rev. 104: 81–120, 1988; Lesley et al. Immunogenetics 22: 149–157, 1985), these results indicate that T cell development in the homozygous transgenic mice is abrogated at a very early stage.

Figure 2D:
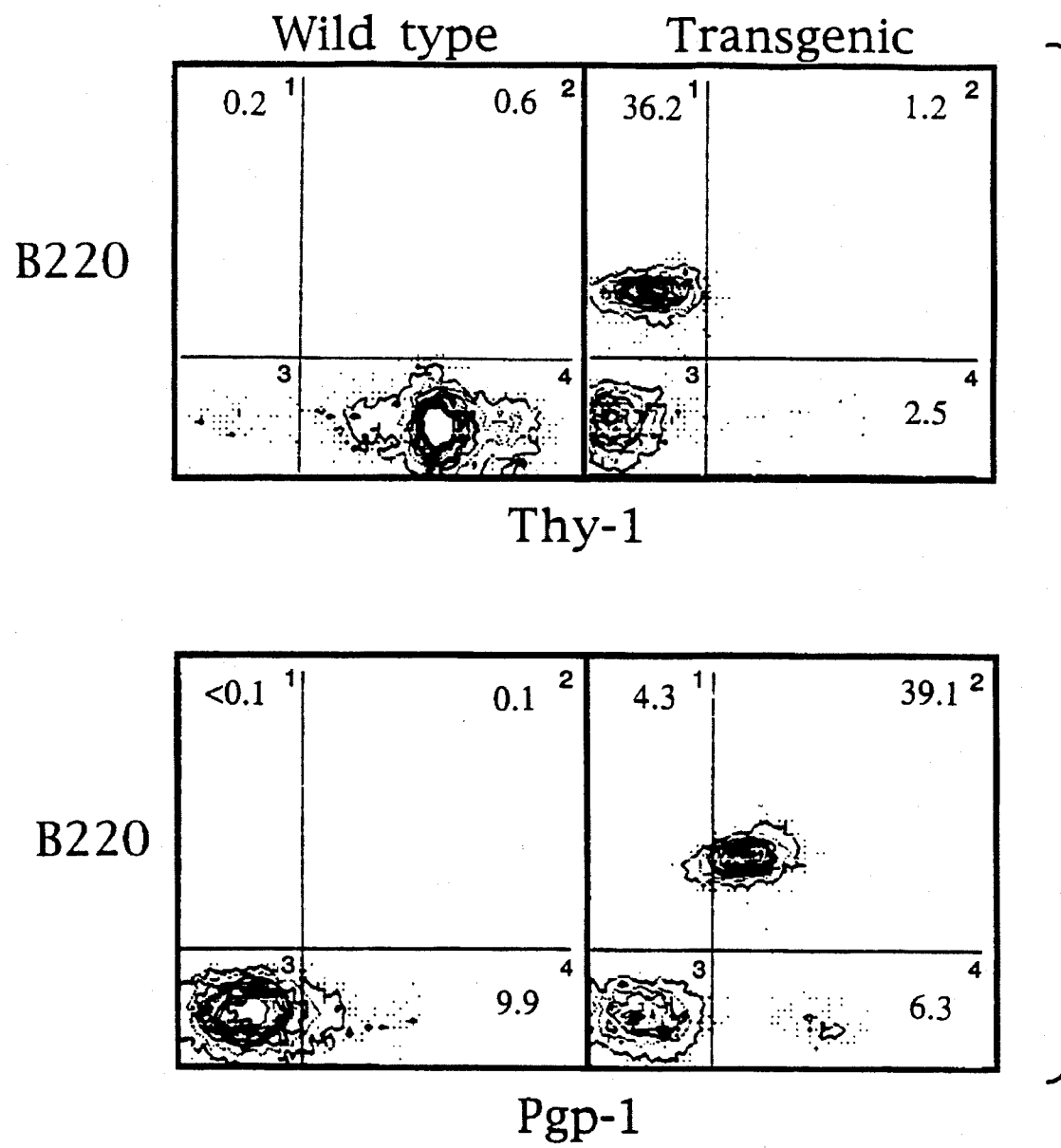
FIG. 2D depicts thymocytes which were double stained with B220 and Thy-1 (top) or B220 and Pgp-1 (bottom). There are large number of B220$^+$ cells (which are also Pgp-1$^+$) in the transgenic thymus.

Interestingly, a large portion of the transgenic lymphocytes were B cells as judged by B220 staining (FIG. 2D). These B cells were also positive for Pgp-1 (FIG. 2D), whereas only a very small population of B cells were detected in the wild type thymus (FIG. 2D). Thus, the increased B cell population appeared to compensate for the loss of T cells in the thymus of the homozygous transgenic mice. Immunohistochemistry analysis of the frozen sections from the homozygous transgenic thymus confirmed that there were considerably larger amount of B cells in the homozygous thymus, and these that B cells formed the most dense lymphocyte patches (FIGS. 3G–H).

Figure 2E:
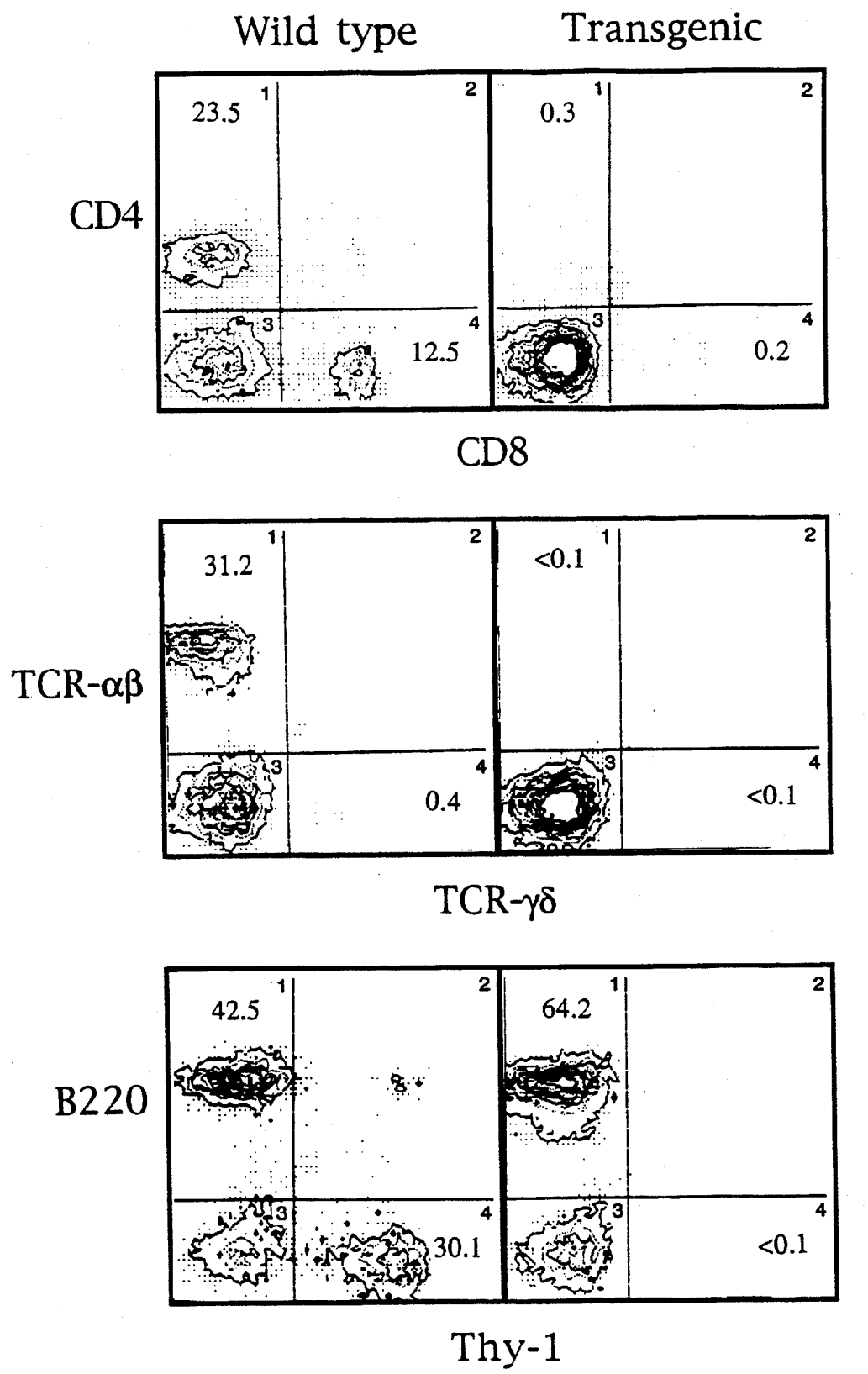
FIG. 2E depicts spleenocytes from transgenic mice and wild type mice which were double stained with following antibodies: CD4 and CD8 (top), TCR-αβ and TCR-γδ (middle, B220 and Thy-1 (bottom). No positive staining for each of these T cell markers (CD4, CD8, TCR-αβ, TCR-γδ and Thy-1) were detected in the transgenic spleenocytes, yet the B220$^+$ cells were increased.

The spleen, the lymph nodes, the peripheral blood lymphocytes (PBL) and the gut lymphocytes were also examined. Although the spleens from homozygous mice were approximately normal in size and total cell number when compared with wild type litter mates, negative staining of the spleen cells with CD4, CD8, CD3, CD5, Thy-1, TCR-αβ and TCR-γδ markers (FIG. 2E) indicated that the spleens of homozygous transgenic mice were also deficient in mature T cells. The loss of T cells was apparently compensated by an increase in B cells (FIG. 2E). The lymph nodes were also found to be normal or slightly smaller in size and total cell number than normal litter mates, but they consisted primarily of B cells with undetectable levels of T lymphocytes. Detectable levels of T cells were also absent in PBL and gut lymphocytes.

The wild type spleen and lymph nodes contain numerous germinal centers which have an outer layer consisting primarily of B cells and an inner center of consisting primarily of T cells. Although there was a normal number of germinal centers in the homozygous spleen, no Thy-1 positive cells could be detected, the cell density in the normal T cell areas was much lower and these cells were B cells. FIG. 3k-1 indicated that there were again no Thy-1 positive cells in the lymph nodes, and the cell density in the normal T cell area was much lower than that in a wild type mouse (FIGS. 3I–L). Furthermore, no T cells were detected in the Payer's patch, while B cells were increased to fulfill the void left by the loss of T cells (FIGS. 3M–P). Therefore, the histological staining further confirmed that the homozygous mice were totally deficient in mature, functionally active T cells.

The heterozygous transgenic line 26 mice showed a more slight degree of T cell deficiency. New-born heterozygous line 26 mice had markedly smaller thymuses than nontransgenic control mice, and microscopic examination of stained paraffin sections revealed almost no cortical thymocytes. However, over the course of the first two weeks after birth, these thymuses developed a near normal architecture, albeit the cell numbers remained about 10–50% of the control mice.

Examination of line 600 homozygous and heterozygous transgenic mice yielded similar results (FIG. 4), indicating that it is unlikely that the T cell deficiency produced by incorporation of the CD3 gene into the mouse genome is due to a position effect. Thus, the development of mature T lymphocytes is abrogated by the introduction of the human CD3-ε gene in the homozygous transgenie mice, and is delayed in the heterozygous mice.

The Arrest of T Cell Development in the Transgenic Mice is Dependent on the Expression of the CD3-ε Protein Northern and Western analyses of the heterozygote transgenic mice demonstrated that the human CD3-ε RNA and protein were expressed specifically in the thymus, spleen and lymph nodes as was the endogenous mouse CD3-ε protein. These results indicated that the abrogation of T cell development in the transgenic mice is not due to a null mutation in the CD3-ε gene, and suggested that the elements regulating CD3-ε expression, such as the enhancers and DNA binding proteins, of the human and mouse CD3-ε gene function in a similar tissue specific manner. Furthermore, the human CD3-ε enhancer, which is located downstream of the last exon contains a number of DNA motifs that are potential binding sites for DNA binding proteins which also regulate TCR-αβ gene expression (Clevers et al. *EMBO J.* 8(9): 2527, 1989). Therefore, it is possible that the abrogation of T cell development in the mutant mice is caused by the introduction of a high copy number of DNA fragments, such as the CD3-ε enhancer, which titrate out the level of DNA binding proteins necessary for proper expression of the mouse CD3-ε and TCR-αβ proteins. Another possibility is that T cell abrogation is caused by a dominant mutation in the CD3-ε signal transduction module of the CD3-ε protein.

Figure 1C:
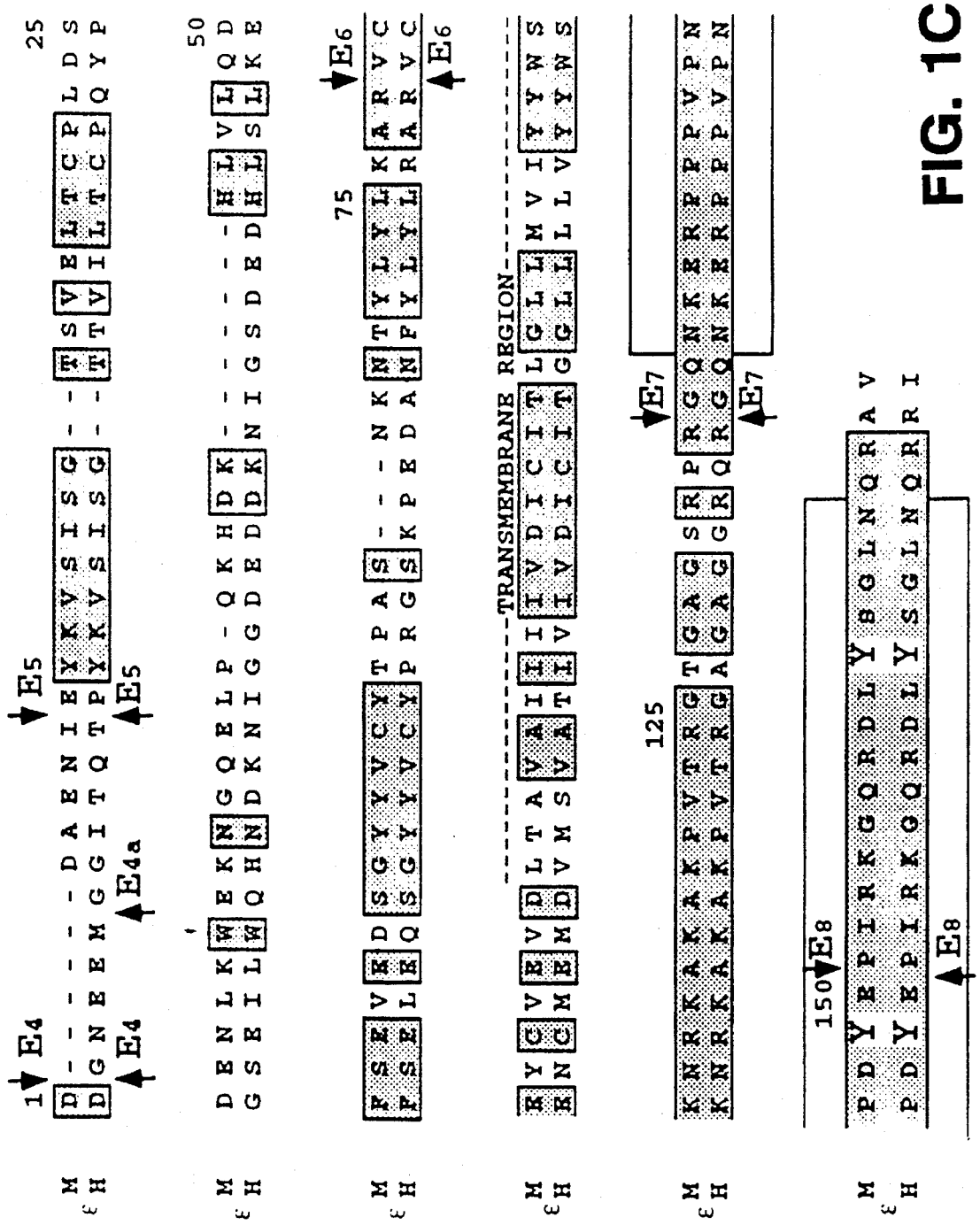

To test these possibilities, transgenic mice bearing an altered form of the human CD3-ε gene were generated. The DNA construct, termed pL12Δ2, was the same as the original pL12 DNA except that a 1.6 kb fragment containing exons 4A to 6, which encode amino acid residues 7–151, was deleted (FIG. 1A). This region includes most of the extracellular domain and the entire transmembrane domain of the CD3-ε protein (FIG. 1C). We hypothesized that: (1) if the presence of the DNA alone can cause an arrest of T cell development, transgenic mice bearing this DNA construct would be deficient in T cells, but (2) if the abrogation of T cell development was due to an alteration in the CD3-ε module, transgenic mice with pL12Δ2 should be normal in T cell development because the protein produced by this construct lacks a transmembrane domain, and thus would not be incorporated into the CD3 complex.

Two stable transgenic lines with high copies of the pL12Δ2DNA were generated: line 2982 (40–45 copies) and line 2944 (20–25 copies). Northern analyses demonstrated that the RNA of the pL12Δ2 construct was expressed in the correct tissue specific manner, however, the mutated protein could not be detected by Western blot or by immunoprecipitation of cell extracts metabolically labelled with $^{14}$C-lysine and $^{14}$C-leucine. T cell development in new-born and adult homozygous, heterozygous transgenic and wild type litter mates was then analyzed by visual inspection of thymus size, determination of the thymocyte numbers, and phenotypic analyses of thymocytes, spleenocytes and lymph nodes cells with CD3, CD4, CD8, TCR-αβ, and Thy1 markers. There were no substantial differences in size or cell number of the thymuses of the homozygous and wild type control mice of both lines (FIG. 4). In addition, staining of T cell markers demonstrated that the transgenic mice had a normal number of mature T cells in the thymus and periphery (FIG. 5 and data not shown). These results suggest that: (1) the deleted 1.6 kb DNA fragment is unlikely to play a role in the regulation of the CD3-ε expression, and (2) the abrogation of T cell development requires the presence of a transgenic CD3-ε protein which is capable of being incorporated into the CD3 complex.

The Abrogation of T Cell Development is Independent of the Presence of the Extracellular Domain of the CD3-ε Protein Once it was established that the CD3-ε protein was required for the induction of the immunodeficiency, we synthesized constructs in order to determine which portions of the CD3-ε protein and the CD3-ε gene were necessary for the promoting the arrest of T cell development.

Since the human CD3-ε protein is expressed in the same cells as the endogenous mouse CD3-ε protein and can form a CD3-εH-εM heterodimer (FIG. 6A; Blumberg et al., 1990, supra), we first tested the possibility that the immunodeficiency was caused by an aberrant signal generated by the CD3-εH-εM heterodimer. Comparison of the amino acid sequences of the human and the mouse CD3-ε proteins, indicates that the cytoplasmic domains differ at only 5 residues (FIG. 1C, Gold 1987 supra), and a recent report has suggested that those 5 residues are not critical for signal transduction (Letourneur 1992, supra). In contrast, the sequences of the mouse and human extracellular CD3-ε domains contain a significant number of differences (FIG. 1C). Thus, it was reasoned that if an aberrant signal were generated via an εH-εM heterodimer, it was likely that the human extracellular domain would play a critical role.

To test this possibility, transgenic mice were generated with another deletion mutation of the human CD3-ε gene. In this construct, pL12Δ1, a 0.6 kb DNA which coded exons 4A and 5 was deleted from the original plasmid pL12 (FIG. 1). This resulted in the deletion of most of the extracellular domain (residues 7–95) (FIG. 1C). Three stable transgenic lines were derived: Line 2978 contained 40–45 copies/cell; line 2966H contained 20–25 copies; and line 2966L contained 3–5 copies.

When these mice were analyzed, it was found that, surprisingly, line 2978 homozygous mice demonstrated a T cell deficiency comparable to that of the line 26 homozygous mice in terms of thymus size, cell number, and in the phenotype of the remaining thymocytes and peripheral T lymphocytes, except that there seemed to have some T cell leakage in the older line 2978 mice (FIGS. 4 and 5). This result indicates that the majority of the human CD3-ε extracellular domain was dispensable, and suggested that the cytoplasmic signal transduction domain was most likely responsible for the T cell deficiency.

High Copy Number of the CD3-ε Gene is Important but not Sufficient for the Induction of the Immunodeficient Phenotype During the analysis of the mice described above, it was observed that there was a dosage-dependent relationship between the phenotype and the copy number of the transgene (FIG. 6B). For example, line 2966H mice (20–25 copies/genome) were also T cell deficient, but to a lesser degree than the line 2978 mice (40–45 copies/genome) (FIGS. 4 and 5), whereas line 2966L (3–5 copies/genome) showed normal T cell development (FIG. 4).

This observation, coupled with the fact that the human and mouse CD3-ε cytoplasmic domains were highly homologous, suggested the possibility that overexpression of the mouse CD3-ε protein would also cause an arrest in T cell development. Accordingly, mice were generated with a chimeric human/mouse CD3-ε gene. This chimeric construct, pL19, contains the portion of the human CD3-ε gene from the 5' upstream sequences through exon 4, and a portion of the mouse CD3-ε mouse sequence from exon 5 through the 3' downstream sequences including the mouse CD3-ε enhancer (FIG. 1). The protein expressed by this chimeric gene is the same as the endogenous mouse CD3-ε protein with the exception of four extracellular residuals at the N-terminus, and thus should function the same as the endogenous mouse protein, while the human sequences at the 5' end of DNA/RNA provide specific markers to distinguish the transgene expression from the endogenous mouse gene expression in Southern and Northern analyses.

A transgenic mouse line (line 3063) with 35–40 copies of the pL19 DNA was generated. Northern analysis indicated that the transgenic RNA was expressed correctly in these mice. The expression of the pL19 protein, which migrates in SDS-PAGE to the same position as the endogenous CD3-ε protein, was then confirmed by an elevated amount (about 1.5 fold) of protein at this position when compared to wild-type litter mates. However, the transgenic mice were found to have a normal T cell development, and the thymuses from homozygous transgenic line 3063 were normal in both size and total cell numbers (FIG. 4). In addition, the phenotypes of the thymocytes and the peripheral T cells were normal, as judged by the staining of the thymocytes, the spleen cells and the lymph node cells with a variety of T cell markers (FIG. 5). These data indicated that the introduction of a high copy number of the mouse CD3-ε gene was insufficient to induce an arrest in T cell development, but did not rule out the possibility that overexpression of the mouse CD3-ε protein is capable of causing abrogation of T cell development, since the level of the total CD3-ε protein in the pL19 line 3036 T cells was determined to be lower than that in the pL12Δ2 line 2978 T cells.

The Role of the Human CD3-ε Enhancer in the Induction of the Immunodeficient Phenotype Comparison of the DNA structures of the pL12Δ1 and the pL19 constructs indicated that part or all of the sequence from exon 5 to 3' end of the human CD3-ε gene is important for the induction of the immunodeficient phenotype. In order to more specifically determine which portion of the human sequence in this region is important for producing the immunodeficiency observed in the pL12Δ1 mice, two lines of transgenic mice were generated which contain chimeric mouse/human CD3-ε genes. One chimeric construct, pL15, contains of the mouse CD3-ε sequence from the 5' upstream sequences through exon 4, and the human CD3-ε sequence from exon 5 to the end of the gene (FIG. 1). The second chimeric construct, pL16, contained the mouse CD3-ε gene from the 5' upstream region through to exon 6, and the human CD3-ε sequence from exon 7 to the end of the gene (FIG. 1).

One transgenic line which contained 100–120 copies/genome of the pL15 DNA, and four lines which contained 10–25 copies/genome of the pL16 DNA were generated. When analyzed as described above for the other transgenic lines, it was found that the mice from each of these lines demonstrated the immunodeficient phenotype (FIGS. 4 and 5).

These results indicate that part or all of the human sequence from exon 7 to the 3' end of the CD3-ε gene is important for the induction of the immunodeficient phenotype. Comparison of the human and mouse sequences in this region shows that only the last two C-terminal amino acid residues of the CD3-ε are different: Arg and Ile in human, compared to Ala and Val in mouse (FIG. 1C). It is unlikely that this difference is responsible for the immunodeficient phenotype, as it has been reported that the two C-terminal residues are not important for signal transduction (LeTourner et al., 1992, supra). However, at the DNA level, the most noticeable difference is between the DNA sequence of the respective CD3-ε enhancers located in the 3' non-coding region of the genes (FIG. 1C). Thus, while the human CD3-ε enhancer functions in the same tissue specific fashion as the mouse counterpart, it appears that the presence of this enhancer region also promotes an over-expression of the CD3-ε transgene which results in a dominant mutation in the CD3-ε signal transduction domain which in turn, produces an immunodeficient phenotype.

The sequences necessary to confer activity of the human CD3-ε enhances have been determined previously by deletion analysis (Clevers et al., EMBO J. 8: 2527, 1989). These experiments demonstrated that the human CD3-ε enhancer contains a small (<125 bp) core at the most 3' end, termed E1, which is indispensable for enhancer activity. This region confers a 5-fold enhancement of CD3-ε expression. The remainder of the enhancer contains regions designated as 'E2' and 'E3' which each amplify enhancer activity 2-fold.

In summary, the above data demonstrates that: 1) the CD3-ε protein is required for the induction of T cell deficiency; 2) the extracellular domain is dispensable for the phenotype; 3) the cytoplasmic domain which contains the signal transduction domain is necessary; 3) overexpression of the protein (e.g., via the presence of the human CD3-ε enhancer) is important, and 4) the phenotype is dependent on the dosage of the transgene.

NK Cell Development is also Impaired in the Transgenic Mice Containing a High Copy Number of the Human CD3-ε Gene Recent studies have indicated that the CD3 proteins are expressed in human NK cells (Lanier et al., J. Immunol. 149: 1876, 1992; Lanier et al., Immunol. Today 13: 392, 1992; Phillips et al., J. Exp. Med. 175: 1055, 1992; Phillips, 1992, supra. Therefore, cytotoxicity assays were performed to assess NK cell activity in homozygous transgenic pL12-26, pL12Δ1-2978 mice, and non-transgenic control mice. The mice were injected 1 day before the assay with 100 μg/mouse polyinosinic:polycytidylic acid (poly I:C), an agent that induces NK cell activity. Spleen cells were isolated and tested for the cytotoxicity against NK-sensitive YAC-1 and NK-resistant EL-4 target cells. As shown in FIG. 7B, homozygous spleen cells from both transgenic lines completely lacked the ability to lyse either YAC-1 or EL-4 target cells at E/T ratios from 7:1 to as high as 200:1, whereas the control spleen cells mediated efficient lysis of YAC-1 cells and some lysis of EL-4 cells. The same observation was made when the spleen cells and the target cells were incubated for 20 hours.

It is also known that NK cells can mediate antibody-dependent cellular cytotoxicity (ADCC) through their Fc receptor (Perussia et al. *J. Exp. Med.* 170: 73–86, 1989). We therefore tested spleen cells from homozygous pL12-26 and control mice for the ability to mediate ADCC using the EL-4 target cell lysis system as described (Rodewald, 1992, supra). EL-4 cells were first coated with 2,4,6-trinitrophenyl (TNP), then stained with a murine monoclonal anti-TNP antibody of the IgG1 isotype, and subsequently used as the target cells for lysis by spleen cells from the homozygous pL12-26 and the control mice. It was found that the spleen cells of the homozygous transgenic mice completely lacked the ability to mediate ADCC, whereas the control spleen cells lysed the target cells efficiently (FIG. 7C). That the cell lysis was due to the action of NK cells was confirmed by the demonstration that ADCC activity could be completely inhibited by addition of the anti-Fc antibody 2.4G2 (FIG. 7C).

To provide further evidence that the homozygous transgenic mice lack NK cell activity, cytotoxic lysis assays were also performed on mice infected with lymphocytic choriomeningitis virus (LMCV), a potent activator of NK cells, as well as against NK-sensitive YAC-1, LE392 and MC57G target cells. As shown in FIG. 8, spleen cells from the homozygous transgenic mice completely lacked the ability to lyse all of the target cells, whereas the control spleen cells mediated lysis efficiently.

In a manner similar to the T cell deficiency in the heterozygous mice, NK cell activity in the heterozygous mice was also reduced. However, there was individual variability in the degree of reduction, and some mice appeared to have near normal NK activity.

Flow cytometric analyses were also conducted to determine if NK cell numbers were depleted in the homozygous mice. We stained the spleen cells with antibodies against cell surface antigens NK1.1, LGL-1, AGM1, as well as HSA (J11d). HSA is expressed on all the immature lymphocytes. LGL-1 and AGM1 are each expressed on a subset of NK cells, whereas the NK1.1 antigen is expressed on all the NK cells from some mouse strains such as B6, but absent from all the NK cells from other mouse stains such as CBA. The results of these experiments showed that, in all control wild type spleens, there were normal numbers of LGL-1$^+$ and AGM-1$^{bright}$ cells. About 50% (6/12) of the control spleens also contained mature NK1.1$^+$AGM-1$^{bright}$ cells, which is consistent with the fact that the transgenic mice were derived from the breeding of B6 and CBA strains. However, mature LGL-1$^+$ and AGM1$^{bright}$ NK cells were absent in all 8 of the transgenic homozygous spleens from pL12-26 and mice which were examined, and NK1.1$^+$ AGM1$^{bright}$ cells were also not detected (FIG. 9). Thus, these results indicated that the mature NK cells are absent in the homozygous mice.

The depletion of the NK cells strongly suggests that the human CD3-ε protein, and possibly the mouse CD3-ε protein, is expressed in the mouse NK cells. To examine this point, Western blot analyses were conducted with an anti-CD3-ε cytoplasmic peptide antibody (DAKO) which can detect both the human and the mouse CD3-ε proteins. The heterozygous pL12Δ1-1978 mice were used for this study because there were considerable amount of NK cells in the heterozygous spleens, and the mouse CD3-ε protein could be easily separated from the transgenic protein. The NK cells were purified by depletion of B cells and T cells from the spleen cells. As a negative control, another heterozygous mouse was treated with anti-AGM1 antibody which depleted NK cells in vivo (Tiberghien et al., Blood 76: 1419, 1990, and the spleen cells were subjected to the same procedures of B cells and T cells depletion.

We found that the mutated human CD3-ε protein was indeed expressed in the purified NK cells (FIG. 10, lane 5). It was further observed that, consistently, in vivo depletion of NK cells virtually abolished the expression of the mutated human protein (FIG. 10, lane 6). However, the endogenous mouse CD3-ε protein was not detected in the NK cells (FIG. 10, lane 5), but was expressed in the T cells (FIG. 10, lane 2). Furthermore, no or a very low level of the mouse CD3-ε protein was detected in the purified NK cells from wild type mouse (FIG. 10, lane 4), in agreement with the previous result that mouse CD3-ε protein was not expressed in the mature murine NK cells (Biron *J. Immunol.* 139(5): 1704–1710, 1987).

It has been reported that while the human CD3-ε protein is not expressed in freshly isolated mature NK cells, expression can be induced by NK cell activation (Lanier et al., 1992, supra). Therefore, we examined mouse spleen cells which were isolated from a wild type mouse and cultured with IL-2 to generate lymphokine activated killer cell (LAK) (Grimm et al., 1983, supra). These LAK cells were NK1.1$^+$ CD3$^-$ as assessed by flow cytometry, but the mouse CD3-ε protein was indeed expressed in these LAK cells (FIG. 10, lane 3).

Taken together, the above data suggest that: (1) the expression of the mouse CD3-ε protein is normally undetectable in freshly isolated murine NK cells, but can be induced by some cytokines such as IL-2, and (2) the overexpression of the human CD3-ε gene in the transgenic mice abrogates NK cell development as well as T cell development.

Generation of Animals with Multiple Immunodeficient Phenotypes

The transgenic animals which are deficient in natural killer cells and T lymphocytes may be used to obtain animals with additional immunodeficient phenotypes. This may be accomplished by combining the genotypes of different animals by cross-breeding the animals containing the different genotypes, or by integrating an appropriate transgene into a zygote or ES cell of an animal.

For example, transgenic animals containing a high copy number of the CD3-ε as described above may be cross-bred with animals which are deficient in B lymphocytes. Alternatively, a high copy number of the CD3-ε gene can be introduced into an embryonic cell of an animal which is deficient in B lymphocytes, or a transgene which is capable of inducing a B cell deficiency may be introduced into an embryonic cell of CD3-ε transgenic mice. A number of animals which are B cell deficient have been generated by disruption of certain genes, e.g., RAG-1 (Mombaerts, et al., *Cell* 68: 869, 1992), RAG-2 (Shinkai et al., *Cell* 68: 855, 1992), and those described in PCT Publication WO92/03918, 1992.

Transgenic animals containing other immunodeficient phenotypes have also been described. These include animals with mutations in IL-2$^-$ (Shorle et al., *Nature* 352: 621, 1991); MHC Class II antigens (Grusby et al., *Science* 35: 253, 1991; Cosgrove et al., *Cell* 66: 1051, 1991); β2-microglobulin (Correa et al., *Proc. Natl. Acad. Sci.* 89: 653, 1992; Pereria et al., *EMBO J.* 11: 25, 1992; Koller et al., *Science* 248: 1247, 1990; Zijlstra et al., *Nature* 344: 742, 1990); TAP- 1 (Kaer et al., *Cell* 71: 1205, 1992) and bcl-1 (Stasser et al., *Cell* 67: 889, 1991). Naturally occurring immunodeficient animals include the nude, SCID, beige and X-linked immunodeficient mice.

Generation of Animal Models

Various protocols can be used to transplant human and other animal cells or tissues into the transgenic animals of the invention. For example, peripheral blood lymphocytes may be transferred to the transgenic animals using standard protocols similar to those described by Mosier et al., (*Science* 251: 791, 1991; and *J. Clin. Immunol.* 10: 185, 1990). Bone marrow tissue may be transplanted using protocols such as the one described by Kamel-Reid (*Science* 246: 1597, 1989). Further, fetal tissue (e.g., human) can be transplanted into the immunodeficient mice of the invention to generate animals with reconstituted immune systems (Kyoizumi et al., *Blood* 79: 1704, 1992; Peault et al., *J. Exp. Med.* 174: 1283, 1991; McCune et al., *Science* 241: 1632, 1988).

USE

The transgenic animals of the invention are superior hosts for xenografts as the combined deficiency in T cells and NK cells not only reduces the rate or frequency of tissue rejection, but also provides increased rate of survival and cell growth of transplanted tissues. In addition, since all cells contain the deficiency, there is no clonal escape of T cells and NK cells as has been observed in both the nude and SCID strains.

Accordingly, the transgenic animals of the invention are especially useful as models for studying the role of human cells in tumorigenesis, transplant rejection, HIV infection, and autoimmune diseases.

In addition, the animals of the invention are useful for diagnostic and therapeutic purposes. For example, animals which contain human immune cells, tumor cells, or other transplanted tissues may be used to test potential therapeutics. In one particular example, animals containing bone marrow cells from a patient with an immunodeficiency, e.g., AIDS, may be used to test compounds for those which are useful for the treatment of the disease.

To test for such useful therapeutics, an animal model for the disease is exposed to the candidate material. Administration is by any known route, but is preferably intravenous, and preferably at a range of concentrations. Following an appropriate period of time, the animal is assessed for the relative progression of the disease compared to untreated control animals (e.g., for the presence of HIV infected cells; for the rate of neoplastic cell growth). A useful therapeutic for treating a disease which produces an immunodeficiency is one which promotes an increase in functionally active immune cells; a useful therapeutic for treating an autoimmune disease is one which promotes tolerance to the autoantigen(s) associated with the disease; and a useful therapeutic for treating cancer tissues is one which arrests the growth of, or kills, the neoplastic cells.

OTHER EMBODIMENTS

The transgenic non-human mammals of the invention may also be made using standard techniques for the stable introduction of DNA into cells. For example, retroviral infection can also be used to introduce transgenes into a non-human animal genome. In one method, developing non-human embryos cultured in vitro to the blastocyst stage may be used as targets for efficient retroviral infection by standard methods (e.g., see Hogan et al., *Manipulating the Mouse Embryo,* CSH Laboratory Press, CSH, NY, 1986).

The animals and models of the invention are also useful for studying the efficacy of various gene therapies for treating immune disorders (e.g., Fleischman, *Am. J. Med. Sci.* 301: 353, 1991; Kelley, *Annals of Internal Med.* 114: 697, 1991.

Cells from the transgenic immunodeficient animals of the invention are also useful as a source of cells for cell culture for the study of immune cell development.

Other embodiments are within the following claims.

---

---

What is claimed is:

1. A transgenic mouse having a substantial deficiency in functionally active natural killer cells and T lymphocytes, wherein the genome of said mouse is characterized by the presence of at least 30 copies of a transgene comprising the cytoplasmic and transmembrane domain encoding regions of a human CD3-ε gene, and said transgene is expressed in the lymphoid tissues of said mouse at levels sufficient to promote said deficiency.

2. The mouse of claim 1, wherein said transgene comprises a DNA encoding the transmembrane and cytoplasmic domains of human CD3-ε operably-linked to a CD3-ε enhancer.

3. The mouse of claim 2, wherein said CD3-ε enhancer is the human CD3-ε enhancer.

4. The mouse of claim 3, wherein said CD3-ε enhancer comprises the E1 domain of the human CD3-ε enhancer.

5. The mouse of claim 4, wherein said CD3-ε enhancer further comprises the E2 domain of the human CD3-ε enhancer.

6. The mouse of claim 3, wherein said enhancer comprises the nucleic acid sequence of SEQ ID NO: 1.

7. The mouse of claim 1, wherein said mouse is further characterized in being substantially deficient in functionally active B lymphocytes.

8. A method of producing a transgenic mouse having a substantial deficiency in functionally active natural killer cells and T lymphocytes, said method comprising, introducing a CD3-ε transgene derived from a human CD3-ε gene into an embryonal cell of a mouse, said transgene encoding at least the cytoplasmic and transmembrane domains of the CD3-ε protein, and said transgene further being capable of promoting a deficiency in natural killer cells and thymocytes, and obtaining progeny containing at least 30 copies of said transgene stably incorporated into the genome and having said deficiency in natural killer cells and T lymphocytes.

9. The method of claim 8 further comprising the step of mating said progeny having said deficiency to produce a transgenic mouse which is homozygous for said transgene.

10. The method of claim 8, wherein said transgene comprises a DNA encoding the E7 and E8 domains of human CD3-ε operably-linked to a CD3-ε enhancer.

11. The method of claim 10, wherein said CD3-ε enhancer is human.

12. The method of claim 11, wherein said CD3-ε enhancer comprises the E1 domain of the human CD3-ε enhancer.

13. The method of claim 12, wherein said CD3-ε enhancer further comprises the E2 domain of the human CD3-ε enhancer.

14. The method of claim 13, wherein said enhancer comprises the nucleic acid sequence of SEQ ID NO: 1.

15. The method of claim 8 wherein said transgene is introduced into an embryonal cell of a mouse which is substantially deficient in B lymphocytes, and said progeny demonstrates a substantial deficiency in natural killer cells, T lymphocytes, and B lymphocytes.

16. The method of claim 15 wherein said embryonal cell is obtained from a mouse which contains a mutation in the RAG-1 gene.

17. The method of claim 15 wherein said embryonal cell is obtained from a mouse which contains a mutation in the RAG-2 gene.

18. The transgenic mouse of claim 1, further comprising human bone marrow cells from a patient with an immune disease.

19. The transgenic mouse of claim 18, wherein said immune disease results in an immunodeficiency.

20. The transgenic mouse of claim 18, wherein said disease is AIDS.

21. The transgenic mouse of claim 18, wherein said immune disease is an autoimmune disease.

22. The transgenic mouse of claim 21, wherein said autoimmune disease is systemic.

23. The transgenic mouse of claim 22, wherein said autoimmune disease is Inflammatory Bowel Disease.

24. The transgenic mouse of claim 21, wherein said autoimmune disease is rheumatoid arthritis.

25. A method of testing a substance for efficacy in the treatment of an immune disease, said method comprising, exposing the mouse of claim 18 to said substance, and determining the progression of said disease in said mouse, an arrest, delay or reversal in said progression as compared to untreated animals being indicative that said substance is useful for the treatment of said immune disease.

26. The transgenic mouse of claim 1, further comprising human neoplastic cells from a patient with a neoplasm.

27. A method of testing the efficacy of an anti-neoplastic therapy, said method comprising, exposing the mouse of claim 26 to said therapy, and determining the progression of said neoplasm in said mouse, an arrest, delay or reversal in said progression as compared to untreated mice being indicative that said substance is useful for the treatment of said neoplasm.

28. The transgenic mouse of claim 1, further comprising a xenograft.

* * * * *

UNITED STATES PATENT AND TRADEMARK OFFICE
CERTIFICATE OF CORRECTION

PATENT NO. : 5,530,179

DATED : June 25, 1996

INVENTOR(S) : Cornelis P. Terhorst and Baoping Wang

It is certified that error appears in the above-identified patent and that said Letters Patent is hereby corrected as shown below:

On the title page, item [75], under "Inventors", replace "Cornelius" with --Cornelis--;

Column 1, line 25,
Under "OTHER PUBLICATIONS", "Clevers et al.", replace "An Enhance Located" with --An Enhancer Located...--;

Column 2, line 15,
Under "OTHER PUBLICATIONS", "Gold et al.", delete "T3 Chains Of The" (second occurrence) before "T-Cell Receptor Complex";

Column 1, line 26,
Under "OTHER PUBLICATIONS", "Marusic-Galesic et al.", replace "$CD4^{31}$" with --$CD4^-$--;

Column 2, lines 22 and 23,
Under "OTHER PUBLICATIONS", "Rodewald et al.", replace "Lymphocytes An Natural Killer Cells" with --Lymphocytes And Natural Killer Cells--;

Column 2, lines 47 and 48,
Under "OTHER PUBLICATIONS, "Van Kaer et al.", replace "$CD4^-8^{30}$" with --$CD4^-8^+$--;

Col. 10, line 45, replace "these that B cells" with --that these B cells--.

Signed and Sealed this

Third Day of December, 1996

BRUCE LEHMAN

Attest:

Attesting Officer     Commissioner of Patents and Trademarks